(12) United States Patent
Klinger et al.

(10) Patent No.: US 6,509,155 B1
(45) Date of Patent: Jan. 21, 2003

(54) NUCLEIC ACIDS ENCODING GTPASE ACTIVATING PROTEINS

(75) Inventors: Tod M. Klinger, San Carlos; Elizabeth A. Stewart, Mountain View; Henry Yue, Sunnyvale; Mariah R. Baughn, San Leandro, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/507,765

(22) Filed: Feb. 18, 2000

(51) Int. Cl.[7] .......................... C12P 21/06; C12Q 1/68; C12N 15/00; C12N 5/00; C07H 21/02; C07H 21/04

(52) U.S. Cl. .................. 435/6; 435/320.1; 435/325; 435/252.3; 435/69.1; 536/23.1; 536/23.5; 536/24.3

(58) Field of Search ................. 536/23.1, 23.5, 536/23.2, 24.3; 435/19, 196, 252.3, 325, 320.1, 69.1, 6; 530/350

(56) References Cited

PUBLICATIONS

Cytoskeleton, Inc. product information for Rho GAP protein, Catalog No. GAP01, 1999.*
GenBank Accession No. Z83838 (Dec. 12, 1999).*
GenBank Accession No. AA514271 (Aug. 18, 1997).*
Aussel et al., "Inhibition and Activation of Interleukin 2 Synthesis by Direct Modification of Guanosine Triphosphate–Binding Proteins", *J. Immunol.*, 140: 215–220 (1988).
Dhanasekaran et al., "Regulation of cell proliferation by G proteins", *Oncegene* 17: 1383–1394(1998).
Kaziro et al., "Structure and Function of Signal–Transducing GTP–Binding Proteins", *Ann Rev Biochem* 60: 349–400(1991).
Tavitian, A., "Proteines Ras et proteines apparentees", *C.R. Seances Soc Biol Fil* 189: 7–12(1995).

Zhang et al., "Characterization of the Interactions between the Small GTPase Cdc42 and Its GTPase–activating Proteins and Putative Effectors", *J. Biol Chem* 272:21999–22007(1997).
Zheng et al., "Biochemical Comparisons of the Saccharomyces cerevisiae Bem2 and Bem3 Proteins", *J Biol Chem* 368: 24629–24634(1993).
Leonard et al., Biochemical Studies of the Mechanism of Action of the Cdc42 *J Biol Chem* 273:16210–16215 (1998).
Fearon et al., "A Genetic Model for Colorectal Tumorigenesis", *Cell* 61:759–767(1990).
Chung et al., "DNA Mismatch Repair and Cancer", *Gastroenterology* 109:1685–1699 (1995).
Castells et al., "Mapping of a Target Region of Allelic Loss to a 0.5–cM Interval on Chromosome 22q13 in Human Colorectal CancerA", *Gastroenterology* 117:8331–837(1999).
Hunt A., (GI 6572185), GenBank Sequence Database (Accession CAB62993), *NCBI* Dec. 12, 1999.
Hall, A., (GI 312212), GenBank Sequence Database (Accession Z23024), *NCBI* Aug. 25, 1997.
Li et al., "Structural Determinants Required for the Interaction between Rho GTPase and the GTPase–activating Domain of p190*", *J Biol Chem* 272: 32830–32835(1997).
Dunham, I. et al., "The DNA sequence of human chromosome 22", *Nature* 402–489–495(1999).

* cited by examiner

*Primary Examiner*—Rebecca E. Prouty
*Assistant Examiner*—D Steadman
(74) *Attorney, Agent, or Firm*—Incyte Genomics, Inc.

(57) ABSTRACT

The invention provides mammalian nucleic acid molecules and fragments thereof. It also provides for the use of the mammalian nucleic acid molecules for the characterization, diagnosis, evaluation, treatment, or prevention of conditions, diseases and disorders associated with cell signaling, the immune system, and cell proliferation, particularly colon cancer. The invention additionally provides expression vectors and host cells for the production of the protein encoded by the mammalian nucleic acid molecules.

13 Claims, 21 Drawing Sheets

5' CAG ACC CGG CAC GCA GGT GGC GGG CGG GGT CCG TGG CCA GAG CTG CAG AGA
   10              19              28              37              46              55

GAC AAG GCG GCG GCG GCT GTG GCT GTG CTG GGT GCA GTG AGG AAG CCC TCG GTG
   64              73              82              91              100             109

GTG CCC ATG GCT GGC CAG GAT CCT GCG CTG AGC ACG AGT CAC CCG TTC TAC GAC
   118             127             136             145             154             163
        M   A   G   Q   D   P   A   L   S   T   S   H   P   F   Y   D

GTG GCC AGA CAT GGC ATT CTG CAG GTG GCA GGG GAT GAC CGC TTT GGA AGA CGT
   172             181             190             199             208             217
    V   A   R   H   G   I   L   Q   V   A   G   D   D   R   F   G   R   R

GTT GTC ACG TTC AGC TGC TGC CGG ATG CCA CCC TCC CAC GAG CTG GAC CAC CAG
   226             235             244             253             262             271
    V   V   T   F   S   C   C   R   M   P   P   S   H   E   L   D   H   Q

CGG CTG GAG TAT TTG AAG TAC ACA CTG GAC CAA TAC GTT GAG AAC GAT TAT
   280             289             298             307             316             325
    R   L   E   Y   L   K   Y   T   L   D   Q   Y   V   E   N   D   Y

FIGURE 1A

| 334 | | 343 | | 352 | | 361 | | 370 | | 379 |
|---|---|---|---|---|---|---|---|---|---|---|
| ACC | ATC | GTC | TAT | TTC | CAC | TAC | GGG | CTG | AAC | AGC | AAC | AAG | CCT | TCC | CTG | GGC |
| T | I | V | Y | F | H | Y | G | L | N | S | N | K | P | S | L | G |

| | | | | 388 | | 397 | | 406 | | 415 | | 424 | | 433 |
|---|---|---|---|---|---|---|---|---|---|---|---|---|---|---|
| TGG | CTC | CAG | AGC | GCA | TAC | AAG | GAG | TTC | GAT | AGG | AAG | TAC | AAG | AAC | TTG | AAG |
| W | L | Q | S | A | Y | K | E | F | D | R | K | Y | K | N | L | K |

| | | | | 442 | | 451 | | 460 | | 469 | | 478 | | 487 |
|---|---|---|---|---|---|---|---|---|---|---|---|---|---|---|
| GCC | CTC | TAC | GTG | GTG | CAC | CCC | ACC | AGC | TTC | ATC | AAG | GTC | CTG | TGG | AAC | ATC | TTG |
| A | L | Y | V | V | H | P | T | S | F | I | K | V | L | W | N | I | L |

| | | | | 496 | | 505 | | 514 | | 523 | | 532 | | 541 |
|---|---|---|---|---|---|---|---|---|---|---|---|---|---|---|
| AAG | CCC | CTC | ATC | AGT | CAC | AAG | TTT | GGG | AAG | AAA | GTC | ATC | TAT | TTC | AAC | TAC | CTG |
| K | P | L | I | S | H | K | F | G | K | K | V | I | Y | F | N | Y | L |

| | | | | 550 | | 559 | | 568 | | 577 | | 586 | | 595 |
|---|---|---|---|---|---|---|---|---|---|---|---|---|---|---|
| AGT | GAG | CTC | CAC | GAA | CAC | CTT | AAA | TAC | GAC | CAG | CTG | GTC | ATC | CCT | CCC | GAA | GTT |
| S | E | L | H | E | H | L | K | Y | D | Q | L | V | I | P | P | E | V |

| | | | | 604 | | 613 | | 622 | | 631 | | 640 | | 649 |
|---|---|---|---|---|---|---|---|---|---|---|---|---|---|---|
| TTG | CGG | TAC | GAT | GAG | AAG | CTC | AGC | CTG | CAG | CAC | GAG | GGC | CGG | ACG | CCG | CCT | CCC |
| L | R | Y | D | E | K | L | S | L | Q | H | E | G | R | T | P | P | P |

FIGURE 1B

```
     658     667     676     685     694     703
ACC AAG ACA CCT CCG CGG CCC CTG CCC ACA CAG CAG TTT GGC GTC AGT
 T   K   T   P   P   R   P   L   P   T   Q   Q   F   G   V   S 712     721     730     739     748     757
CTG CAA TAC CTC AAA GAC AAA AAT CAA GGC GAA CTC ATC CCC CCT GTG CTG AGG
 L   Q   Y   L   K   D   K   N   Q   G   E   L   I   P   P   V   L   R 766     775     784     793     802     811
TTC ACA GTG ACG TAC AGA GAG AAA GGC CTG CGC ACC GAG GGC CTG TTC CGG
 F   T   V   T   Y   R   E   K   G   L   R   T   E   G   L   F   R 820     829     838     847     856     865
AGA TCC GCC AGC GTG CAG ACC GTC GAG CGC CAG AGG CTC TAC AAC CAA GGG
 R   S   A   S   V   Q   T   V   E   R   Q   R   L   Y   N   Q   G 874     883     892     901     910     919
AAG CCC GTG AAC TTT GAC GAC TAC GGG GAC ATT CAC CAG ATC CCT GCC GTG ATC CTG
 K   P   V   N   F   D   D   Y   G   D   I   H   Q   I   P   A   V   I   L 928     937     946     955     964     973
AAG ACC TTC CTG CGA GAG CTG CCC CAG CCG CTT CTG ACC TTC CAG GCC TAC GAG
 K   T   F   L   R   E   L   P   Q   P   L   L   T   F   Q   A   Y   E
```

FIGURE 1C

```
      982         991         1000        1009        1018        1027
CAG ATT CTC GGG ATC ACC TGT GTG GAG AGC AGC CTG CGT GTC ACT GGC TGC CGC
 Q   I   L   G   I   T   C   V   E   S   S   L   R   V   T   G   C   R 1036        1045        1054        1063        1072        1081
CAG ATC TTA CGG AGC CTC CCA AAC TAC GTC CTC CGC TAC CTC ATG
 Q   I   L   R   S   L   P   N   Y   V   L   R   Y   L   M 1090        1099        1108        1117        1126        1135
GGC TTC CTG CAT GCG GTG TCC CGG GAG AGC ATC TTC AAC AAA ATG AAC AGC TCT
 G   F   L   H   A   V   S   R   E   S   I   F   N   K   M   N   S   S 1144        1153        1162        1171        1180        1189
AAC CTG GCC TGT GTC TTC GGG CTG AAT TTG ATC TGG CCA TCC CAG GGG GTC TCC
 N   L   A   C   V   F   G   L   N   L   I   W   P   S   Q   G   V   S 1198        1207        1216        1225        1234        1243
TCC CTG AGT GCC CTT GTG CCC AAC ATG TTC ACT GAA CTG CTG ATC GAG TAC
 S   L   S   A   L   V   P   N   M   F   T   E   L   L   I   E   Y 1252        1261        1270        1279        1288        1297
TAT GAA AAG ATC TTC AGC ACC CCG GAG GCA CCT GGG GAG CAC GGC CTG GCA CCA
 Y   E   K   I   F   S   T   P   E   A   P   G   E   H   G   L   A   P
```

FIGURE 1D

```
       1306         1315         1324         1333         1342         1351
TGG GAA CAG GGG AGC AGG GCA GCC CCT TTG CAG GAG GCT GTG CCA CGG ACA CAA
 W   E   Q   G   S   R   A   A   P   L   Q   E   A   V   P   R   T   Q 1360         1369         1378         1387         1396         1405
GCC ACG GGC CTC ACC AAG CCT ACC CTA CCT CCG AGT CCC CTG ATG GCA GCC AGA
 A   T   G   L   T   K   P   T   L   P   P   S   P   L   M   A   A   R 1414         1423         1432         1441         1450         1459
AGA CGT CTC TAG TGT TGC GAA CAC TCT GTA TAT TTC GAG CTA CCT CCC ACA CCT
 R   R   L 1468         1477         1486         1495         1504         1513
GTC TGT GCA CTT GTA TGT TTT ATA AAC TTG GCA TCT GTA AAA ATA ACC AGC CAT 1522         1531         1540         1549
TAG ATG AAT TCA GAA CCT TCT AAT GAA AAA AAA AAA 3'
```

FIGURE 1E

```
5'  AGA  CCC  GGC  ACG  CAG  GTG  GGG  GCC  GGC  GGG  GTC  CGT  GGA  CCA  GAG  CTG  CAG  AGA
     1         11             20             29             38             47         56

GAC  AAG  GCG  GCG  GCT  GTG  GCT  GTG  GCT  CTG  GGT  GCA  GTG  AGG  AAG  CCC  TCG  GTG
              65             74             83             92            101            110

GTG  CCC  ATG  GCT  GGC  GCG  CAG  GAT  CCT  GCG  CTG  AGC  ACG  AGT  CAC  TTC  TAC  GAC
             119            128            137            146            155            164
              M    A    G    Q    D    P    A    L    S    T    S    H    F    Y    D

GTG  GCC  AGA  CAT  TTC  AGC  ATT  CTG  CAG  GTG  GCA  GGG  GAT  GAC  CGC  TTT  GGA  AGA  CGT
             173            182            191            200            209            218
              R    H    F    S    I    L    Q    V    A    G    D    D    R    F    G    R    R

GTT  GTC  GCC  ACG  TTC  AGC  TGC  CGG  ATG  CCA  CCC  TCC  CAC  GAG  CTG  GAC  CAC  CAG
             227            236            245            254            263            272
              V    V    A    T    F    S    C    R    M    P    P    S    H    E    L    D    H    Q

CGG  CTG  GAG  TAT  TTG  AAG  TAC  ACA  CTG  GAC  CAA  TAC  GTT  GAG  AAC  GAT  TAT
             281            290            299            308            317            326
              R    L    E    Y    L    K    Y    T    L    D    Q    Y    V    E    N    D    Y
```

FIGURE 2A

```
ACC ATC GTC TAT TTC CAC TAC GGG CTG AAC AGC CGG AAC AAG CCT TCC CTG GGC
335         344         353         362         371         380
 T   I   V   Y   F   H   Y   G   L   N   S   R   N   K   P   S   L   G

TGG CTC CAG AGC GCA TAC AAG GAG TTC GAT AGG AAG TAC AAG AAC TTG AAG
389         398         407         416         425         434
 W   L   Q   S   A   Y   K   E   F   D   R   K   Y   K   N   L   K

GCC CTC TAC GTG GTG CAC CCC ACC AGC CCC TTC ATC AAG GTC CTG TGG AAC ATC TTG
443         452         461         470         479         488
 A   L   Y   V   V   H   P   T   S   F   I   K   V   L   W   N   I   L

AAG CCC CTC ATC AGT CAC CAC AAG TTT GGG AAG AAA GTC ATC TAT TTC AAC TAC CTG
497         506         515         524         533         542
 K   P   L   I   S   H   H   K   F   G   K   K   V   I   Y   F   N   Y   L

AGT GAG CTC CAC GAA CAC CTT AAA TAC GAC CAG CTG GTC ATC CCT CCC GAA GTT
551         560         569         578         587         596
 S   E   L   H   E   H   L   K   Y   D   Q   L   V   I   P   P   E   V

TTG CGG TAC GAT GAG AAG CTC CAG AGC CTG CAC GAG GGC CGG ACG CCG CCT CCC
605         614         623         632         641         650
 L   R   Y   D   E   K   L   Q   S   L   H   E   G   R   T   P   P   P
```

FIGURE 2B

```
    659         668         677         686         695         704
ACC AAG ACA CCA CCG CGG CCC CTG CCC ACA CAG CAG TTT GGC GTC AGT
 T   K   T   P   P   R   P   L   P   T   Q   Q   F   G   V   S
    713         722         731         740         749         758
CTG CAA TAC CTC AAA GAC AAA AAT CAA GGC GAA CTC ATC CCC CTG AGG
 L   Q   Y   L   K   D   K   N   Q   G   E   L   I   P   L   R
    767         776         785         794         803         812
TTC ACA GTG ACG TAC CTG AGA GAG AAA GGC CTG CGC ACC GAG GGC TTC
 F   T   V   T   Y   L   R   E   K   G   L   R   T   E   G   F
    821         830         839         848         857         866
AGA TCC GCC AGC GTG CAG CAG ACC GTC CGC GAG ATC CAG AGG CTC TAC AAC CAA GGG
 R   S   A   S   V   Q   Q   T   V   R   E   I   Q   R   L   Y   N   Q   G
    875         884         893         902         911         920
AAG CCC GTG AAC TTT GAC GAC TAC GGG GAC ATT CAC CCT GCC GTG ATC CTG
 K   P   V   N   F   D   D   Y   G   D   I   H   P   A   V   I   L
    929         938         947         956         965         974
AAG ACC TTC CTG CGA GAG CTG CCC CAG CCG CTT CTG ACC TTC CAG GCC TAC GAG
 K   T   F   L   R   E   L   P   Q   P   L   L   T   F   Q   A   Y   E
```

FIGURE 2C

```
      983                992           1001          1010          1019          1028
CAG ATT CTC GGG ATC ACC TGT GTG GAG AGC AGC CTG CGC GTC ACT CGC TGC CGC
 Q   I   L   G   I   T   C   V   E   S   S   L   R   V   T   R   C   R 1037               1046          1055          1064          1073          1082
CAG ATC TTA CGG AGC CTC CCA GAG CAC AAC TAC GTC CTC CGC TAC CTC ATG
 Q   I   L   R   S   L   P   E   H   N   Y   V   L   R   Y   L   M 1091               1100          1109          1118          1127          1136
GGC TTC CTG CAT GCG GTG TCC CGG GAG AGC ATC TTC AAC AAA ATG AAC AGC TCT
 G   F   L   H   A   V   S   R   E   S   I   F   N   K   M   N   S   S 1145               1154          1163          1172          1181          1190
AAC CTG GCC TGT GTC TTC GGG CTG AAT TTG ATC TGG CCA TCC CAG GGG GTC TCC
 N   L   A   C   V   F   G   L   N   L   I   W   P   S   Q   G   V   S 1199               1208          1217          1226          1235          1244
TCC CTG AGT GCC CTT GTG CCC CTG AAC ATG TTC ACT GAA CTG CTG ATC GAG TAC
 S   L   S   A   L   V   P   L   N   M   F   T   E   L   L   I   E   Y 1253               1262          1271          1280          1289          1298
TAT GAA AAG ATC TTC AGC ACC CCG GAG GCA CCT GGG GAG CAC GGC CTG GCA CCA
 Y   E   K   I   F   S   T   P   E   A   P   G   E   H   G   L   A   P

FIGURE 2D
```

```
      1307              1316              1325              1334              1343              1352
TGG GAA CAG GGG AGC AGG GCA GCC CCT TTG CAG GAG GCT GTG CCA CGG ACA CAA
 W   E   Q   G   S   R   A   A   P   L   Q   E   A   V   P   R   T   Q 1361              1370              1379              1388              1397              1406
GCC ACG GGC CTC ACC AAG CCT CTA CCT CCG AGT CCC CTG ATG GCA GCC AGA
 A   T   G   L   T   K   P   L   P   P   S   P   L   M   A   A   R 1415              1424              1433              1442              1451              1460
AGA CGT CTC TAG TGT TGC GAA CAC TCT GTA TGT TTC GAG CTA CCT CCC ACA CCT
 R   R   L 1469              1478              1487              1496              1505              1514
GTC TGT GCA CTT GTA TGT TTT GTA AAC TTG GCA TCT GTA AAA ATA ACC AGC CAT 1523              1532
TAG ATG AAT TCA GAA CCT TCT AAT G 3'
```

FIGURE 2E

| | | | | |
|---|---|---|---|---|
| 1 | [M A] - - - - - - - - - - - - - - - - - - - - - - - - - - - - - - - - - - - - - | 404424 |
| 1 | [M A] - - - - - - - - - - - - - - - - - - - - - - - - - - - - - - - - - - - - - | 3068538 |
| 1 | - - - - - - - - - - - - - - - - - - - - - - - - - - - - - - - - - - - - - - - | g6572185 |
| 1 | [M] D P L S E L Q D D L T L D D T S E A L N Q L K L A S I D E | g312212 |

| | | |
|---|---|---|
| 3 | - - - - - - - - - - - - - - - - - - - - - - - - - [G Q D P A L S T] - - - - - | 404424 |
| 3 | - - - - - - - - - - - - - - - - - - - - - - - - - [G Q D P A L S T] - - - - - | 3068538 |
| 1 | - - - - - - - - - - - - - - - - - - - - - - - - - - - - - - - - - - - - - - - | g6572185 |
| 31 | K N W P S D E M P D F P K S D D S K S S S [P E] L V [T H] L K W | g312212 |

| | | |
|---|---|---|
| 11 | S H P F Y D V A R H G I L Q V A G D D R F G R R V V T F S C | 404424 |
| 11 | S H P F Y D V A R H G I L Q V A G D D R F G R R V V T F S C | 3068538 |
| 1 | - - - - - - - - - - - - - - - - - - - - - - - - - - - - - - - - - - - - - - - | g6572185 |
| 61 | D D [P Y] D I A R H [Q] I [V E] V A G D D K Y G R K I I V F S [A] | g312212 |

| | | |
|---|---|---|
| 41 | C R M P P S H E L D H Q R L L E Y L K Y T L D Q Y V E N D Y | 404424 |
| 41 | C R M P P S H E L D H Q R L L E Y L K Y T L D Q Y V E N D Y | 3068538 |
| 1 | - - - - - - - - - - - - - - - - - - - - - - - - - - - - - - - - - - - - - - - | g6572185 |
| 91 | C R M P P S H [Q L] D H [S K] L [L] G Y L [K H] T L D Q Y V E [S] D Y | g312212 |

| | | |
|---|---|---|
| 71 | T I V Y F H Y G L N S R N K P S L G W L Q S A Y K E F D R K | 404424 |
| 71 | T I V Y F H Y G L N S R N K P S L G W L Q S A Y K E F D R K | 3068538 |
| 1 | - - - - - - - - - - - - - - - - - - - - - - - - - - - - - - - - - - - - - - - | g6572185 |
| 121 | [T] L L [Y] L [H] H G L T S [D N] K P S L [S W] L R D A Y R E F D R K | g312212 |

|     |                                  |          |
|-----|----------------------------------|----------|
| 250 | G K P V N F D D Y G D I H I P A V I L K T F L R E L P Q P L | 404424 |
| 250 | G K P V N F D D Y G D I H I P A V I L K T F L R E L P Q P L | 3068538 |
| 150 | G K P V N F D D Y G D I H I P A V I L K T F L R E L P Q P L | g6572185 |
| 300 | G L P V D F D Q Y N E L H L P A V I L K T F L R E L P E P L | g312212 |

|     |                                  |          |
|-----|----------------------------------|----------|
| 280 | L T F Q A Y E Q I L G I T C V E S S L R V T R C R Q I L R S | 404424 |
| 280 | L T F Q A Y E Q I L G I T C V E S S L R V T G C R Q I L R S | 3068538 |
| 180 | L T F Q A Y E Q I L G I T C V E S S L R V T G C R Q I L R S | g6572185 |
| 330 | L T F D L Y P H V V G F L N I D E S Q R V P A T L Q V L Q T | g312212 |

|     |                                  |          |
|-----|----------------------------------|----------|
| 310 | L P E H N Y V V L R Y L M G F L H A V S R E S I F N K M N S | 404424 |
| 310 | L P E H N Y V V L R Y L M G F L H A V S R E S I F N K M N S | 3068538 |
| 210 | L P E H N Y V V L R Y L M G F L H A V S R E S I F N K M N S | g6572185 |
| 360 | L P E E N Y Q V L R F L T A F L V Q I S A H S D Q N K M T N | g312212 |

|     |                                  |          |
|-----|----------------------------------|----------|
| 340 | S N L A C V F G L N L I W P S Q G V S S L S A L V P L N M F | 404424 |
| 340 | S N L A C V F G L N L I W P S Q G V S S L S A L V P L N M F | 3068538 |
| 240 | S N L A C V F G L N L I W P S Q G V S S L S A L V P L N M F | g6572185 |
| 390 | T N L A V V F G P N L L W A K D A A I T L K A I N P I N T F | g312212 |

FIGURE 3C

| | | |
|---|---|---|
| 370 | T E L L I E Y Y E K I F S T P E A P G E H G L A P W E Q G S | 404424 |
| 370 | T E L L I E Y Y E K I F S T P E A P G E H G L A P W E Q G S | 3068538 |
| 270 | T E L L I E Y Y E K I F S T P E A P G E H G L A P W E Q G S | g6572185 |
| 420 | T K F L L D H Q G E L F P S P D P S G - - - - - - - - - - | g312212 |
| 400 | R A A P L Q E A V P R T Q A T G L T K P T L P P S P L M A A | 404424 |
| 400 | R A A P L Q E A V P R T Q A T G L T K P T L P P S P L M A A | 3068538 |
| 300 | R A A P L Q E A V P R T Q A T G L T K P T L P P S P L M A A | g6572185 |
| 439 | - - - - - - - - - - - - - - - - - - - - - - - - - - - | g312212 |
| 430 | R R R L | 404424 |
| 430 | R R R L | 3068538 |
| 330 | R R R L | g6572185 |
| 439 | - - - L | g312212 |

FIGURE 3D

```
404424.5         caagacaccaccacgccgcgcggccccccgctgcccacacagcagtttggcgtcagtctgcaatacctcaaagac
3068538CB1       caagacacctccgccgcgcggccccccgctgcccacacagcagtttggcgtcagtctgcaatacctcaaagac
2465422F6        caagaaacttcggcgg*ggncccccggtgcc.........................................
2631247F6        caagacaccaccacgccgcgcggccccccgctgcccacacagcagtttggcgtcagtctgcaatacctcaaagac
957130X313V1     caagacaccacctccgccgcgcggccccccgctgcccacacagcagtttggcgtcagtctgcaatacctcaaagac
1580628H1        caagacancaccgccgcgcggccccccgctgcccananagcagtttggcgtcagtctgcaatacctcaaa...
1580545H1        caagacaccaccgccgcgcggccccccgctgcccacacagcagtttggcgtcagtctgcaatacctcaa....
1891457H1        caagacaccaccacgccgcgcggcctccgctgcccacacagcagtttggcgtcagtctgcaatacctcaaagac
4649657H1        .....................................agcagtttggcgtcagtctgcaatacctcaaagac
                           660         670         680         690        700         710       720
```

FIGURE 4A

```
                                ▽                                   ▽
              GAGCAGCCTGCGCGTCA*CTCGCTGCCGCCAGAT*CTTACGGAGCCTCCCAGAGCACAACTACGTCGTCC
404424.5      GAGCAGCCTGCGCGTGTca*ctggctgCCGCCAGAT*CTTACGGAGCCTCCCAGAGCACAACTACGTCGTCC
3068538CB1    na*cagc*tncgtgtaa*tt*gnttccgccn*at*nttacg*agc*tcccagagcanaa*tangt*gtcc
957130X313V1  GAGCAGCCTGCGCGTGTca*ctggctgccgc*agattcttacGGAGCCTCCCAGAGCACAACTACGTCGTCC
908465R2      gAGCAGCCTGCGCGTGTca*ctggctgcngccagat*cttacggngcctcccaggacncaactacgtngtcc
4002758H1     GAGCAGCCTGCGCGTGTca*ctggctgCCGCCAGAT*CTTACGGAGCCTCCCAGAGCACAACTACGTCGTCC
957130R6      GAGCAGCCTGCGCGTGTca*ctggctgCCGCCAGAT*CTTACGGAGCCTCCCAGAGCACAACTACGTCGTCC
957130R1      GAGCAGCCTGCGCGTGTca*ctggctgCCGCCAGAT*CTTACGGAGCCTCCCAGAGCACAACTACGTCGTCC
957130H1      GAGCAGCCTGCGCGTGTca*ctggctgCCGCCAGAT*CTTACGGAGCCTCCCAGAGCACAACTACGTCGTCC
2624365T6.comp GAGCAGCCTGCGCGTCA*CTCGCTGCCGCCAGAT*CTTACGGAGCCTCCCAGAGCACAACTACGTCGTCC
2044444H1     GAGCAGCCTGCGCGTCA*CTCGCTGCCGCCAGAT*CTTACGGAGCCTCCCAGAGCACAACTACGTCGTCC
3416883T6.comp GAGCAGCCTGCGCGTgtcaact*gctgCCGCCAGAT*CTtacg*agcCTCCCAGagcCTCCCAGAGCACAACTACGTCGTCC
1301520T6.comp ttccagcCTGCGCGTGTca*ct*gntgccGCCAGAT*CTTACGGAGCCTCCCAGAGCACAACTACGTCGTCC
1301520H1     ...cagcCTGCGCGTGTca*ctggctgCCGCCAGAT*CTTACGGAGCCTCCCAGAGCACAACTACGTCGTCC
1301520F6     ...cagcCTGCGCGTGTca*ctggctgCCGCCAGAT*CTTACGGAGCCTCCCAGAGCACAACTACGTCGTCC
1422635X305D1 ........c*antgntgccgcaagat**ttacggagcntcccagAGCACAACTACGTCGTCC
.comp
              ........ △ ......|.........|.........|.........|.........|.........|.........|
                       1010     1020      1030      1040      1050      1060      1070
```

FIGURE 4B

```
7012449926H1   ..........................................ccggcctgccctggggccagccaggtgtgcggctagagtagctgagatcaggagaggtgc
7009950169H2   ..................................ctggggccagccaggtgtgcggctagagtagctgagatcaggagaggtgc
3068538CB1     ..........................gcagacccggcacgcaggtggggcccggggtccgtggc
                                            80          90         100         110         120         130         140

7012449926H1   tcggtggaccgagctgcagagacaaggaagcagcagccacactgagggccacaggagaccctcagtggt
7009950169H2   tcggtggtccgagctgcagagacaaggaagcagcagccacactgagggccacaggagaccctcagtggt
3068538CB1     cagagctgcagagacaaggacgggcggcgctgtgctgggtgcagtgaggaagaggccctcggtggt
                           150         160         170         180         190         200         210

7012449926H1   gttcatggcctggacccccacgctgagcactgagcacaagtcacccattctatgatgtggccagacggcatc
7009950169H2   gttcatggcctggacccccacgctgagcactgagcacaagtcacccattctatgatgtggccagtcacgcatc
3068538CB1     gcccatggctgccaggatcctgcgctgcgagcacgagtcctacgttctacgactgtggccagacatggcatt
                           220         230         240         250         260         270         280

7012449926H1   ctgcaggtggcag...............................................
7009950169H2   ctgcaggtggcaggggatgaccgccagggagacgcatcttcacttttcagctgctgccggttgccaccct
3068538CB1     gcccaggtggcaggggaggggatgaccgcttttggaagacgtgttgtcacgttcacgttcagctgccgatgccaccct
                      290         300         310         320         330         340         350

7012449926H1   tgcaccagctcaa.................................................
3068538CB1     cccacgagctggaccaccagagcgctgctgagtattgaagtacacactggaccaatacgttgagaacga
7015759974H1   ..............................................................
7004480528H1   ..............................................................
7009935753H1   ..............................................................
7009936061H1   ..............................................................
                      370         380         390         400         410         420
```

FIGURE 5A

```
3068538CB1      ttataccatcgtctattccactacgggctgaacagccgaacaagccttccctgggctggctccagagc
7015759974H1    ....................................................................
7004805281H1    ....................................................................
7009357753H1    ....................................................................
7009360611H1    ....................................................................
                          .         .         .         .         .         .         .
                         430       440       450       460       470       480       490

3068538CB1      gcatacaaggagttcgataggaagtacaagaagaacttgaaggccctctacgtggtgcaccccaccagct
7015759974H1    .....................................................................
7004805281H1    .....................................................................
7009357753H1    .....................................................................
7009360611H1    .....................................................................
                          .         .         .         .         .         .         .
                         500       510       520       530       540       550       560

3068538CB1      tcatcaaggtcctgtggaacatcttgaagccctcatcagtcacaagtttgggaagaaagtcatctattt
7015759974H1    .....................................................................
7004805281H1    .....................................................................
7009357753H1    .....................................................................
7009360611H1    .....................................................................
                          .         .         .         .         .         .         .
                         570       580       590       600       610       620       630

3068538CB1      caactacctgagtgagctccacgaacaccttaaatacgaccagctggtcatccctcccgaagttttgcgg
7015759974H1    .....................................................................
7004805281H1    .....................................................................
7009357753H1    .....................................................................
7009360611H1    .....................................................................
                          .         .         .         .         .         .         .
                         640       650       660       670       680       690       700
```

FIGURE 5B

```
3068538CB1       tacgatgagaagctccagagcctgcacgagggccgcgcctcccaccaagacacctccgcgcggc
7015759741H1     ................................................................
7004805281H1     ................................................................
7012740361H1     .........................................cagccctcccaccaagacgccgccacctcggc
7009357531H1     ................................................................
7009360611H1     ................................................................
                                                    710       720       730       740       750       760       770

3068538CB1       cccgctgcccacacagcagtttggcgtcagtctgcaatacctcaaagacaaaatcaaggcgaactcat
7015759741H1     cgcctctgcctaccagtcagttccggcgtcagtttgcaatacctcagagacaaaaatcaaggtgaactcat
7004805281H1     ................................................................
7012740361H1     ...........................................................atcaaggtgaactcat
7009357531H1     ................................................................
7009360611H1     ................................................................
                                                    780       790       800       810       820       830       840

3068538CB1       cccccctgtgctgaggttcacagtgactgtacctgagagagaaggcctgcgcaccgagggcctgttccgg
7015759741H1     cccccctgtgctgcttgcgttggacgttggacatatctgagagagaaaaaaggactgcacactgaagcctgttccgg
7004805281H1     cccccctgtgctg...................................................
7012740361H1     ................................................................
7009357531H1     ................................................................
7009360611H1     ................................................................
                                                    850       860       870       880       890       900       910

3068538CB1       agatccgccagcgtgcagacccgtccgcgagatccagaggctctacaaccaagggaagcccgtgaactttg
7015759741H1     agatcagcagcgccagactgtccgccaggtcagcggctctatgatcaaggaagcctgtgaactttg
7004805281H1     ................................................................
7012740361H1     ................................................................
7009357531H1     ...........................................................aagggaagcctgtgaactttg
7009360611H1     ................................................................
                                                    920       930       940       950       960       970       980
```

FIGURE 5C

```
3068538CB1      acgactacggggacattcacatccctgcgtgatcctgaagaccttcctgcgagagctgccccagccgct
7015759747H1    atgattatggtgacatgcacctcccagctcccagctgtgattcttgagagacattttcttcgaagagctgccccagccact
7012740361H1    atgattatggngacatgcacctcccagctgtgattctaaagacattcttcgaagagctgccccagccact
7004805281H1
7009357531H1
7009360611H1
                                990       1000      1010      1020      1030      1040      1050

3068538CB1      tctgaccttccaggcctacgagcagattctcgggatccacctgtgtggagagcagcctgcgtgtcactggc
7015759747H1    gctgaccttcca.......
7012740361H1    gctgaccttccaagcntacgagcagattctcgggatcaccagtgtggagagcagcctgcg......
7004805281H1
7009357531H1
7009360611H1
                                1060      1070      1080      1090      1100      1110      1120

3068538CB1      tgccgccagatcttacggagcctcccagagcacaactacgtcgtcctccgctacctcatgggcttcctgc
7015759747H1
7012740361H1
7004805281H1                    cctgaggagcctcccagagcacaactacgtcctccgctacctcatgggcttcctgc
7009357531H1
7009360611H1
                                1130      1140      1150      1160      1170      1180      1190

3068538CB1      atgcggtgtcccggggagagcatcttcaa*caaaatgaacagctctaacctggcctgtcttcgggctga
7015759747H1
7012740361H1
7004805281H1    atgaggtgtctctggagagcat....t*tccaaacaagatgaacagctctaacctggcatgtgttgttgggctg.
7009357531H1                    t*ttcaaacaagatgaacagctctaacctggcatgtgttgttgggctga
7009360611H1                    t*ttcaaacaagatgaacagctctaacctggcatgtgttgttgggctga
                                1200      1210      1220      1230      1240      1250      1260
```

FIGURE 5D

```
3068538CB1   atttgatctggccatcccaggggggtctcctccctgagtgcccttgtgcccctgaacatgttcactgaact
7015975974H1 ......................................................................
7004480528H1 ..acttgatctggccatcccaggggggtgcttccctgagcgcccctggttcctctgaacttgttcacagagct
7009335753H1 ..acttgatctggccatcccaggggggtggctcccctgagcgccctggttcctctgaacttgttcacagagct
7009336061H1 ..acttgatctggccatcccaggggggtggctcccctgagcgccctggttcctctgaacttgttcacagagct
                1270      1280      1290      1300      1310      1320      1330

3068538CB1   gctgatcgagtactatga*aaagatctcttcagcaccccggaggcacctggggagcacggcctggccaccatg
7015975974H1 ......................................................................
7004480528H1 ......................................................................
7009335753H1 gctgatagagtactatgacaaag*tcttcagtgcccaggagggcctggggagcacatccggatactgt
7009336061H1 gctgatagagtactatgacaaag*tcttcagtgcccaggagggcctggggagcacatccggatactgt
                1340      1350      1360      1370      1380      1390      1400

3068538CB1   ggaacagggggagcaggcagcccctttgcaggaggctgtgccacggacacaagccacgggcctcaccaag
7015975974H1 ......................................................................
7004480528H1 ......................................................................
7009335753H1 cgaaacgaaacaggcctggtcctgtt............................................
7009336061H1 cgaaacgaaacaggctggtcctgttaccaagaattcacacagacgggcactcccgggcctca........
                1410      1420      1430      1440      1450      1460      1470
```

FIGURE 5E

SEQUENCE LISTING

<160> NUMBER OF SEQ ID NOS: 33

<210> SEQ ID NO 1
<211> LENGTH: 476
<212> TYPE: DNA
<213> ORGANISM: Homo sapiens
<220> FEATURE:

-continued

```
<221> NAME/KEY: misc_feature
<223> OTHER INFORMATION: Incyte ID No: 908465R2
<220> FEATURE:
<221> NAME/KEY: unsure
<222> LOCATION: 314, 343, 446
<223> OTHER INFORMATION: a, t, c, g, or other

<400> SEQUENCE: 1
ctctcctgca ggcctgcgca ccgagggcct gttccggaga tccgccagcg tgcagaccgt      60
ccgcgagatc cagaggctct acaaccaagg gaagcccgtg aactttgacg actacgggga    120
cattcacatc cctgccgtga tcctgaagac cttcctgcga gagctgcccc agccgcttct    180
gaccttccag gcctacgagc agattctcgg gatcacctgt gtggagagca gcctgcgtgt    240
cactggctgc cgcagattct tacggagcct cccagagcac aactacgtcg tcctccgcta    300
cctcatgggc ttcntgcatg cggtgtcccg ggagagcatc ttnaacaaaa tgaacagctc    360
taacctggcc tgtgtcttcg ggctgaattt gatctggcat ccaggggtc tcctcctga     420 gtgcccttgt gcccctgaac atgttnactg aactgctgat cgagtactat gaaaag        476

<210> SEQ ID NO 2
<211> LENGTH: 321
<212> TYPE: DNA
<213> ORGANISM: Homo sapiens
<220> FEATURE:
<221> NAME/KEY: misc_feature
<223> OTHER INFORMATION: Incyte ID No: 957130R6

<400> SEQUENCE: 2
cagagctgtc cttcctacac ccctgttctc ctcccgggcc gggatgcagc gctgcccctg      60
gcccctctgg agctcagcag ggagccccat gcccttccag gtgtggagag cagcctgcgt    120
gtcactggct gccgccagat cttacggagc ctcccagagc acaactacgt cgtcctccgc    180
tacctcatgg gcttcctgca tgcggtgtcc cgggagagca tcttcaacaa aatgaacagc    240
tctaacctgg cctgtgtctt cgggctgaat ttgatctggc catcccaggg ggtctcctcc    300
ctgagtgccc ttgtgccccct g                                              321

<210> SEQ ID NO 3
<211> LENGTH: 195
<212> TYPE: DNA
<213> ORGANISM: Homo sapiens
<220> FEATURE:
<221> NAME/KEY: misc_feature
<223> OTHER INFORMATION: Incyte ID No: 1580628H1
<220> FEATURE:
<221> NAME/KEY: unsure
<222> LOCATION: 85, 96, 98, 102-103, 106, 108, 136, 161, 163
<223> OTHER INFORMATION: a, t, c, g, or other

<400> SEQUENCE: 3
atctatttca actacctgag tgagctccac gaacaccttta aatacgacca gctggtcatc      60
cctcccgaag ttttgcggta cgatnagaag ctccanancc tnnacnangg ccggacgccg    120
cctcccacca agacancacc gccgcggccc ccgctgccca nanagcagtt tggcgtcagt    180
ctgcaatacc tcaaa                                                       195

<210> SEQ ID NO 4
<211> LENGTH: 487
<212> TYPE: DNA
<213> ORGANISM: Homo sapiens
<220> FEATURE:
<221> NAME/KEY: misc_feature
<223> OTHER INFORMATION: Incyte ID No: 2631247F6
```

```
<220> FEATURE:
<221> NAME/KEY: unsure
<222> LOCATION: 483
<223> OTHER INFORMATION: a, t, c, g, or other

<400> SEQUENCE: 4
ccggaacaag ccttccctgg gctggctcca gagcgcatac aaggagttcg ataggaagta      60
caagaagaac ttgaaggccc tctacgtggt gcacccacc agcttcatca aggtcctgtg     120
gaacatcttg aagccctca tcagtcacaa gtttgggaag aaagtcatct atttcaacta     180
cctgagtgag ctccacgaac accttaaata cgaccagctg gtcatcctc ccgaagtttt     240 gcggtacgat gagaagctcc agagcctgca cgagggccgg acgccgcctc ccaccaagac     300
accaccgccg cggcccccgc tgcccacaca gcagtttggc gtcagtctgc aatacctcaa     360
agacaaaaat caaggcgaac tcatccccc tgtgctgagg ttcacagtga cgtacctgag     420
agagaaaggc ctgcgcaccg agggcctgtt ccggagattc ggccagcgtg cagaccgtcc     480 gcngaga                                                             487

<210> SEQ ID NO 5
<211> LENGTH: 259
<212> TYPE: DNA
<213> ORGANISM: Homo sapiens
<220> FEATURE:
<221> NAME/KEY: misc_feature
<223> OTHER INFORMATION: Incyte ID No: 3068538H1
<220> FEATURE:
<221> NAME/KEY: unsure
<222> LOCATION: 9, 17, 33, 39, 41, 48, 51, 86, 158, 198, 200, 219, 228
<223> OTHER INFORMATION: a, t, c, g, or other

<400> SEQUENCE: 5
gcacgtggng gccggcnggg tccgtggcca canctgcana nacacaangc ngcggcggct      60
gctgtgctgg gtgcagtgag gaacangcc tcggtggtgc ccatggctgg ccaggatcct     120
gcgctgagca cgagtcaccc gttctacgac gtggccanac atggcattct gcaggtggca     180
ggggatgacc gctttggnan acgtgttgtc acgttcagnt gctgccgnat gccaccctcc     240
cacgagctgg accaccagc                                                  259

<210> SEQ ID NO 6
<211> LENGTH: 388
<212> TYPE: DNA
<213> ORGANISM: Homo sapiens
<220> FEATURE:
<221> NAME/KEY: misc_feature
<223> OTHER INFORMATION: Incyte ID No: 3532286T6
<220> FEATURE:
<221> NAME/KEY: unsure
<222> LOCATION: 6, 9, 17, 23, 40, 65, 72, 77, 103, 171, 188, 193, 208,
                216,
<222> LOCATION: 231, 247, 272, 274, 301, 346, 364, 382
<223> OTHER INFORMATION: a, t, c, g, or other

<400> SEQUENCE: 6
acaggngtng gaggtanctc canacacagt gttcgcaacn ctagagacgt cttctggctg      60
ccatnagggg antcggnggt agggtaggct tggtgaggcc cgnggcttgt gtccgtggca     120
cagcctcctg caaaggggct gccctgttcc cctgttccca tggtgccagg ncgtgctccc     180
caggtgcntc canggtgctg aagatctntt catagnactc gatcagcagc ncagtgaaca     240
tgttcanggg cacaagggca ctcagggagg anancccctg ggatggccag atcaaattca     300
ncccgaagac acaggccagg ttagagctgt tcattttgtt gaagangctc tcccgggaca     360
```
ccgnatgcag gaagcccatg angtagcg                                          388

<210> SEQ ID NO 7
<211> LENGTH: 512
<212> TYPE: DNA
<213> ORGANISM: Homo sapiens
<220> FEATURE:
<221> NAME/KEY: misc_feature
<223> OTHER INFORMATION: Incyte ID No: 1301520F6
<220> FEATURE:
<221> NAME/KEY: unsure
<222> LOCATION: 452, 471
<223> OTHER INFORMATION: a, t, c, g, or other

<400> SEQUENCE: 7
cagcctgcgt gtcactggct gccgccagat cttacggagc ctcccagagc acaactacgt    60
cgtcctccgc tacctcatgg gcttcctgca tgcggtgtcc cgggagagca tcttcaacaa   120
aatgaacagc tctaacctgg cctgtgtctt cgggctgaat tgatctggc catcccaggg    180 ggtctcctcc ctgagtgccc ttgtgcccct gaacatgttc actgaactgc tgatcgagta   240
ctatgaaaag atcttcagca ccccggaggc acctggggag cacggcctgg caccatggga   300
acaggggagc agggcagccc ctttgcagga ggctgtgcca cggacacaag cccacgggcc   360
tcaccaagcc taacctactc cgagtcccct gatggcagcc agaagacgtc tctagtgttg   420
cgaacactct gtatatttcg agctactccc anaactgtct gtgacttgta ngttttataa   480
acttggcatc tgtaaaaata accagcatta ga                                 512

<210> SEQ ID NO 8
<211> LENGTH: 480
<212> TYPE: DNA
<213> ORGANISM: Homo sapiens
<220> FEATURE:
<221> NAME/KEY: misc_feature
<223> OTHER INFORMATION: Incyte ID No: 2465422F6
<220> FEATURE:
<221> NAME/KEY: unsure
<222> LOCATION: 2, 221, 368, 470
<223> OTHER INFORMATION: a, t, c, g, or other

<400> SEQUENCE: 8
angcgctgca ggcatgcctg gcggggggcag caggtgaggg gtcctgattt tccccgagtt    60
tatttcattc tttgtttgat gtccttaaat tgatcctgtt gagaggagta acattctgag   120
actcacagtg gaggcagctg tttcagggtt attgggcgtg gggtgtttct cggagcgcgg   180
cagcctgaag tcatcccccg tttccctcct caggtacaag nagaacttga aggccctcta   240
cgtggtgcac ccccaccagc ttcatcaagg tcctgtggaa catcttgaag ccctcatca   300 gtcacaagtt tgggaagaaa gtcatctatt tcaactacct gagtgagctc cacgaacacc   360
ttaaatanga ccagctggtc atccctcccg aagttttgcg gtacgatgag aactccagag   420
cctgcacgag ggccgggacg gcggcttcca acaagaaact tcggcggggn ccccggtgcc   480

<210> SEQ ID NO 9
<211> LENGTH: 655
<212> TYPE: DNA
<213> ORGANISM: Homo sapiens
<220> FEATURE:
<221> NAME/KEY: misc_feature
<223> OTHER INFORMATION: Incyte ID No: 957130X313V1
<220> FEATURE:
<221> NAME/KEY: unsure
<222> LOCATION: 352, 425, 437-438, 440, 479, 481, 486, 493, 504, 512,
           515,
<222> LOCATION: 534, 539, 550, 591, 603, 617, 623, 625, 630, 633, 640, 649
<223> OTHER INFORMATION: a, t, c, g, or other

<400> SEQUENCE: 9

```
gtttgggaag aaagtcatct atttcaacta cctgagtgag ctccacgaac accttaaata        60
cgaccagctg gtcatccctc ccgaagtttt gcggtacgat gagaagctcc agagcctgca       120
cgagggccgg acgccgcctc ccaccaagac acctccgccg cggcccccgc tgcccacaca       180
gcagtttggc gtcagtctgc aatacctcaa agacaaaaat caaggcgaac tcatcccccc       240
tgtgctgggg ttcacagtga cgtactgaga gagaaaggcc tgcgcaccga ggggctgttc       300
cggagattcg ccaacgtgta gaccgtcgcg aaattcagag gtctacaacc angggagcct       360
gtgaactttg acgactacgg gggcattcac atccctgccg tgatcctgaa gaccttcctg       420
gaganttgcc caagcgnntn ttaccttcca ggcctacgag aaattctcgg ggatcactnt       480
nttganacag ctncgtgtaa ttgnttccgc cnatnttacg agctcccaga gcanaatang       540
tgtccttcgn tacctcatgg gtcctcatcg gtgtccggga agatttcaaa naaaatgaaa       600
gtntaactgg ctttgtntcg ggntnaattn atntggcaan ccaaggggnt ccccc           655
```

<210> SEQ ID NO 10
<211> LENGTH: 194
<212> TYPE: DNA
<213> ORGANISM: Homo sapiens
<220> FEATURE:
<221> NAME/KEY: misc_feature
<223> OTHER INFORMATION: Incyte ID No: 1580545H1
<220> FEATURE:
<221> NAME/KEY: unsure
<222> LOCATION: 161
<223> OTHER INFORMATION: a, t, c, g, or other

<400> SEQUENCE: 10

```
atctatttca actacctgag tgagctccac gaacacctta aatacgacca gctggtcatc        60
cctcccgaag ttttgcggta cgatgagaag ctccagagcc tgcacgaggg ccggacgccg       120
cctcccacca agacaccacc gccgcggccc ccgctgccca nacagcagtt tggcgtcagt       180
ctgcaatacc tcaa                                                         194
```

<210> SEQ ID NO 11
<211> LENGTH: 281
<212> TYPE: DNA
<213> ORGANISM: Homo sapiens
<220> FEATURE:
<221> NAME/KEY: misc_feature
<223> OTHER INFORMATION: Incyte ID No: 1891457H1

<400> SEQUENCE: 11

```
gctggtcatc cctcccgaag ttttgcggta cgatgagaag ctccagagcc tgcacgaggg        60
ccggacgccg cctcccacca agacaccacc gccgcggcct ccgctgccca cacagcagtt       120
tggcgtcagt ctgcaatacc tcaaagacaa aaatcaaggc gaactcatcc ccctgtgct        180
gaggttcaca gtgacgtacc tgagagagaa aggcctgcgc accgagggcc tgttccggag       240
atccgccagc gtgcagaccg tccgcgagat ccagaggctc t                           281
```

<210> SEQ ID NO 12
<211> LENGTH: 268
<212> TYPE: DNA
<213> ORGANISM: Homo sapiens
<220> FEATURE:
<221> NAME/KEY: misc_feature
<223> OTHER INFORMATION: Incyte ID No: 4649657H1

<220> FEATURE:
<221> NAME/KEY: unsure
<222> LOCATION: 251
<223> OTHER INFORMATION: a, t, c, g, or other

<400> SEQUENCE: 12

```
agcagtttgg cgtcagtctg caatacctca aagacaaaaa tcaaggcgaa tcatcccccc      60
tgtgctgagg ttcacagtga cgtacctgag agagaaaggc ctgcgcaccg agggcctgtt     120
ccggagatcc gccagcgtgc agaccgtccg cgagatccag aggctctaca accaagggaa     180
gcccgtgaac tttgacgact acggggacat tcacatccct gccgtgatcc tgaagacctt    240
cctgcgagag ntgccccagc cgcttctg                                        268
```

<210> SEQ ID NO 13
<211> LENGTH: 271
<212> TYPE: DNA
<213> ORGANISM: Homo sapiens
<220> FEATURE:
<221> NAME/KEY: misc_feature
<223> OTHER INFORMATION: Incyte ID No: 4002758H1
<220> FEATURE:
<221> NAME/KEY: unsure
<222> LOCATION: 8, 75, 120, 163, 178, 191, 201, 256, 265
<223> OTHER INFORMATION: a, t, c, g, or other

<400> SEQUENCE: 13

```
gggaagcncg tgaactttga cgactacggg gacattcaca tccctgccgt gatcctgaag      60
accttcctgc gaganctgcc ccagccgctt ctgaccttcc aggcctacga gcagattctn    120
gggatcacct gtatggagag cagcctgcgt gtcactggct gcngccagat cttacggngc    180
ctcccaggac ncaactacgt ngtcctccgc tacctcatgg gcttcctgca tgcggtgtcc    240
agggagagca tcttcnacaa aatgnacagc t                                    271
```

<210> SEQ ID NO 14
<211> LENGTH: 488
<212> TYPE: DNA
<213> ORGANISM: Homo sapiens
<220> FEATURE:
<221> NAME/KEY: misc_feature
<223> OTHER INFORMATION: Incyte ID No: 957130R1
<220> FEATURE:
<221> NAME/KEY: unsure
<222> LOCATION: 387, 441, 479
<223> OTHER INFORMATION: a, t, c, g, or other

<400> SEQUENCE: 14

```
cagagctgtc cttcctacac ccctgttctc ctcccgggcc gggatgcagc gctgcccctg      60
gcccctctgg agctcagcag ggagccccat gcccttccag gtgtggagag cagcctgcgt    120
gtcactggct gccgccagat cttacggagc ctcccagagc acaactacgt cgtcctccgc    180
tacctcatgg gcttcctgca tgcggtgtcc cgggagagca tcttcaacaa aatgaacagc    240
tctaacctgg cctgtgtctt cgggctgaat ttgatctggc catcccaggg ggtctcctcc    300
ctgagtgccc ttgtgcccct gaacatgttc actgaactgc tgatcgagta ctatgaaaag    360
atcttcagca ccccggaggc acctggngag cacggcctgg caccatggga cagggggagc    420
agggcagccc ctttgcagga ngctgtgcac ggacacaagc cacgggctca acaagctanc    480
ctacctcg                                                              488
```

<210> SEQ ID NO 15
<211> LENGTH: 567
<212> TYPE: DNA

<213> ORGANISM: Homo sapiens
<220> FEATURE:
<221> NAME/KEY: misc_feature
<223> OTHER INFORMATION: Incyte ID No: 2624365T6

<400> SEQUENCE: 15

```
acagatgcca agtttacaaa acatacaagt gcacagacag gtgtgggagg tagctcgaaa      60
catacagagt gttcgcaaca ctagagacgt cttctggctg ccatcagggg actcggaggt     120
agggtaggct tggtgaggcc cgtggcttgt gtccgtggca cagcctcctg caaaggggct     180
gccctgctcc cctgttccca tggtgccagg ccgtgctccc cacgtgcctc cggggtgctg     240
aagatctttt catagtactc gatcagcagt tcagtgaaca tgttcagggg cacaagggca     300
ctcagggagg agacccnctg ggatggccag atcaaattca gcccgaagac acaggccagg     360
ttagagctgt tcattttgtt gaagatgctc tcccgggaca ccgcatgcag gaagcccatg     420
aggtagcgga ggacgacgta gttgtgctct gggaggctcc gtaagatctg gcggcagcga     480
gtgacgcgca ggctgctctc cacacaggtg atcccgagaa tctgctcgta ggcctggaag     540
gtcagaagcg gctggggcag ctctcgc                                          567
```

<210> SEQ ID NO 16
<211> LENGTH: 265
<212> TYPE: DNA
<213> ORGANISM: Homo sapiens
<220> FEATURE:
<221> NAME/KEY: misc_feature
<223> OTHER INFORMATION: Incyte ID No: 2044444H1

<400> SEQUENCE: 16

```
gcgagagctg ccccagccgc ttctgacctt ccaggcctac gagcagattc tcgggatcac      60
ctgtgtggag agcagcctgc gcgtcactcg ctgccgccag atcttacgga gcctcccaga     120
gcacaactac gtcgtcctcc gctacctcat gggcttcctg catgcggtgt cccgggagag     180
catcttcaac aaaatgaaca gctctaacct ggcctgtgtc ttcgggctga atttgatctg     240
gccatcccag ggggtctcct ccctg                                            265
```

<210> SEQ ID NO 17
<211> LENGTH: 518
<212> TYPE: DNA
<213> ORGANISM: Homo sapiens
<220> FEATURE:
<221> NAME/KEY: misc_feature
<223> OTHER INFORMATION: Incyte ID No: 3416883T6
<220> FEATURE:
<221> NAME/KEY: unsure
<222> LOCATION: 496
<223> OTHER INFORMATION: a, t, c, g, or other

<400> SEQUENCE: 17

```
tacaaaacat acaagtgcac agacaggtgt gggaggtagc tcgaaacata cagagtgttc      60
gcaacactag agacgtcttc tggctgccat caggggactc ggaggtaggg taggcttggt     120
gaggcccgtg gcttgtgtcc gtggcacagc ctcctgcaaa ggggctgccc tgctcccctg     180
ttcccatggt gccaggccgt gctccccagg tgcctccggg gtgctgaaga tcttttcata     240
gtactcgatc agcagttcag tgaacatgtt caggggcaca agggcactca gggaggagac     300
cccctgggat ggccagatca aattcagccc gaagacacag gccaggttag agctgttcat     360
tttgttgaag atgctctccc gggacaccgc atgcaggaag cccatgaggt agcggaggac     420
gacgtattgt gctctgggag gctcgtaaga tctggcggca gcagttgaca cgcaggctgc     480
```

```
tctccacacc tggaanggca tggggctccc tgctgagc                              518
```

```
<210> SEQ ID NO 18
<211> LENGTH: 548
<212> TYPE: DNA
<213> ORGANISM: Homo sapiens
<220> FEATURE:
<221> NAME/KEY: misc_feature
<223> OTHER INFORMATION: Incyte ID No: 1301520T6
<220> FEATURE:
<221> NAME/KEY: unsure
<222> LOCATION: 509
<223> OTHER INFORMATION: a, t, c, g, or other

<400> SEQUENCE: 18
ggttctgaat tcatctaatg gctggttatt tttacagatg ccaagtttat aaaacataca      60
agtgcacaga caggtgtggg aggtagctcg aaatatacag agtgttcgca acactagaga    120
cgtcttctgg ctgccatcag gggactcgga ggtaggtag gcttggtgag gcccgtggct    180
tgtgtccgtg gcacagcctc ctgcaaaggg gctgccctgc tcccctgttc ccatggtgcc    240
aggccgtgct ccccaggtgc ctccggggtg ctgaagatct tttcatagta ctcgatcagc    300
agttcagtga acatgttcag gggcacaagg gcactcaggg aggagacccc ctgggatggc    360
cagatcaaat tcagcccgaa gacacaggcc aggttagagc tgttcatttt gttgaagatg    420
ctctcccggg acaccgcatg caggaagccc atgaggtagc ggaggacgac gtattgtgct    480
ctgggaggct ccgtaagatc tggcggcanc agtgacacgc aggctggaat tcgaattccg    540
agcttacg                                                              548
```

```
<210> SEQ ID NO 19
<211> LENGTH: 244
<212> TYPE: DNA
<213> ORGANISM: Homo sapiens
<220> FEATURE:
<221> NAME/KEY: misc_feature
<223> OTHER INFORMATION: Incyte ID No: 1301520H1

<400> SEQUENCE: 19
cagcctgcgt gtcactggct gccgccagat cttacggagc ctcccagagc acaactacgt     60
cgtcctccgc tacctcatgg gcttcctgca tgcggtgtcc cgggagagca tcttcaacaa    120
aatgaacagc tctaacctgg cctgtgtctt cgggctgaat ttgatctggc catcccaggg    180
ggtctcctcc ctgagtgccc ttgtgcccct gaacatgttc actgaactgc tgatcgagta    240
ctat                                                                  244
```

```
<210> SEQ ID NO 20
<211> LENGTH: 521
<212> TYPE: DNA
<213> ORGANISM: Homo sapiens
<220> FEATURE:
<221> NAME/KEY: misc_feature
<223> OTHER INFORMATION: Incyte ID No: 1422635X305D1
<220> FEATURE:
<221> NAME/KEY: unsure
<222> LOCATION: 495, 516, 519
<223> OTHER INFORMATION: a, t, c, g, or other

<400> SEQUENCE: 20
cattagaagg ttctgaattc atctaatggc tggttatttt tacagatgcc agtttacaa      60
aacatacaag tgcacagaca ggtgtgggag gtagctcgaa acatacagag tgttcgcaac    120
actagagacg tcttctggct gccatcaggg gactcggagg tagggtaggc ttggtgaggc    180
```

```
ccgtggcttg tgtccgtggc acagcctcct gcaaaggggc tgccctgctc ccctgttccc    240
atggtgccag gccgtgctcc ccaggtgcct ccggggtgct gaagatcttt tcatagtact    300
cgatcagcag ttcagtgaac atgttcaggg gcacaagggc actcagggag agacccccct    360
gggatggcca gatcaaattc agcccgaaga cacaggccag gttagagctg ttcattttgt    420
tgaagatgct ctcccgggac accgcatgca ggagcccatg aggtagcgga ggacgacgta    480
gttgtgctct gggangctcc gtaaatcttg cggcancant g                        521
```

<210> SEQ ID NO 21
<211> LENGTH: 213
<212> TYPE: DNA
<213> ORGANISM: Rattus norvegicus
<220> FEATURE:
<221> NAME/KEY: misc_feature
<223> OTHER INFORMATION: Incyte ID No: 701244926H1

<400> SEQUENCE: 21

```
ccggcctgcc ctggggccag ccaggtgtgc ggctagagta gctgagatca ggagaggtgc     60
tcggtggacc gagctgcaga gacaaggaag cagcagccac actgagggcc acaggaggac    120
cctcagtggt gttcatggct ggcctggacc ccacgctgag cacaagtcac ccattctatg    180
atgtggccag acacggcatc ctgcaggtgg cag                                 213
```

<210> SEQ ID NO 22
<211> LENGTH: 273
<212> TYPE: DNA
<213> ORGANISM: Rattus norvegicus
<220> FEATURE:
<221> NAME/KEY: misc_feature
<223> OTHER INFORMATION: Incyte ID No: 700950169H2

<400> SEQUENCE: 22

```
ctggggccag ccaggtgtgc ggctagagta gctgagatca ggagaggtgc tcggtggtcc     60
gagctgcaga gacaaggaag cagcagccac actgagggcc acaggaggac cctcagtggt    120
gttcatggct ggcctggacc ccacgctgag cacaagtcac ccattctatg atgtggccag    180
tcacggcatc ctgcaggtgg caggggatga ccgccagggg agacgcatct tcactttcag    240
ctgctgccgg ttgccaccct tgcaccagct caa                                 273
```

<210> SEQ ID NO 23
<211> LENGTH: 325
<212> TYPE: DNA
<213> ORGANISM: Rattus norvegicus
<220> FEATURE:
<221> NAME/KEY: misc_feature
<223> OTHER INFORMATION: Incyte ID No: 701575974H1

<400> SEQUENCE: 23

```
cagcccctcc caccaagacg ccgccacctc ggccgcctct gcctacccag cagttcggcg     60
tcagtttgca atacctcaga gacaaaaatc aaggtgaact catcccccct gtgctgcgtt    120
ggacggtgac atatctgaga gaaaaaggac tgcacactga aggcctgttc cggagatcag    180
ccagcgccca gactgtccgc caggtgcagc ggctctatga tcaagggaag cctgtgaact    240
ttgatgatta tggtgacatg cacctcccag ctgtgattct aaagacattt cttcgagagc    300
tgccccagcc actgctgacc ttcca                                          325
```

<210> SEQ ID NO 24
<211> LENGTH: 233
<212> TYPE: DNA

<213> ORGANISM: Rattus norvegicus
<220> FEATURE:
<221> NAME/KEY: misc_feature
<223> OTHER INFORMATION: Incyte ID No: 701274036H1

<400> SEQUENCE: 24

```
atcaaggtga actcatcccc cctgtgctgc gttggacggt gacatatctg agagaaaaag      60
ggaagcctgt gaactttgat gattatggcg acatgcacct cccagctgtg attctaaaga     120
catttcttcg agagctgccc cagccactgc tgaccttcca agcctacgag cagattctcg     180
ggatcaccag tgtggagagc agcctgcgag tgacccactg ccgcctgatc ctg            233
```

<210> SEQ ID NO 25
<211> LENGTH: 128
<212> TYPE: DNA
<213> ORGANISM: Rattus norvegicus
<220> FEATURE:
<221> NAME/KEY: misc_feature
<223> OTHER INFORMATION: Incyte ID No: 700480528H1

<400> SEQUENCE: 25

```
cctgaggagc ctcccagaac acaactatgc cgtcctccgc tacctcatgg gcttcctgca      60
tgaggtgtct ctggagagca ttccaaacaa gatgaacagc tctaacctgg catgtgtgtt     120
tgggctga                                                              128
```

<210> SEQ ID NO 26
<211> LENGTH: 212
<212> TYPE: DNA
<213> ORGANISM: Rattus norvegicus
<220> FEATURE:
<221> NAME/KEY: misc_feature
<223> OTHER INFORMATION: Incyte ID No: 700935753H1

<400> SEQUENCE: 26

```
tttcaaacaa gatgaacagc tctaacctgg catgtgtgtt tgggctgaac ttgatctggc      60
catcccaggg ggtggcttcc ctgagcgccc tggttcctct gaacttgttc acagagctgc     120
tgatagagta ctatgacaaa gtcttcagtg cccaggaggg ccctggggag cacatccggg     180
atactgtcga aacgaaacag gctggtcctg tt                                   212
```

<210> SEQ ID NO 27
<211> LENGTH: 251
<212> TYPE: DNA
<213> ORGANISM: Rattus norvegicus
<220> FEATURE:
<221> NAME/KEY: misc_feature
<223> OTHER INFORMATION: Incyte ID No: 700936061H1

<400> SEQUENCE: 27

```
tttcaaacaa gatgaacagc tctaacctgg catgtgtgtt tgggctgaac ttgatctggc      60
catcccaggg ggtggcttcc ctgagcgccc tggttcctct gaacttgttc acagagctgc     120
tgatagagta ctatgacaaa gtcttcagtg cccaggaggg ccctggggag cacatccggg     180
atactgtcga aacgaaacag gctggtcctg ttaccaaaga attcacacag acgggcactc     240
cccgggcctc a                                                          251
```

<210> SEQ ID NO 28
<211> LENGTH: 1549
<212> TYPE: DNA
<213> ORGANISM: Homo sapiens
<220> FEATURE:
<221> NAME/KEY: misc_feature -continued
<223> OTHER INFORMATION: Incyte ID No: 3068538CB1

<400> SEQUENCE: 28

| | | | | | |
|---|---|---|---|---|---|
| gcagacccgg | cacgcaggtg | ggggccggcg | gggtccgtgg | ccagagctgc | agagagacaa | 60 |
| ggcggcggcg | gctgctgtgc | tgggtgcagt | gaggaagagg | ccctcggtgg | tgcccatggc | 120 |
| tggccaggat | cctgcgctga | gcacgagtca | cccgttctac | gacgtggcca | gacatggcat | 180 |
| tctgcaggtg | gcaggggatg | accgctttgg | aagacgtgtt | gtcacgttca | gctgctgccg | 240 |
| gatgccaccc | tcccacgagc | tggaccacca | gcggctgctg | gagtatttga | agtacacact | 300 |
| ggaccaatac | gttgagaacg | attataccat | cgtctatttc | cactacgggc | tgaacagccg | 360 |
| gaacaagcct | tccctgggct | ggctccagag | cgcatacaag | gagttcgata | ggaagtacaa | 420 |
| gaagaacttg | aaggccctct | acgtggtgca | ccccaccagc | ttcatcaagg | tcctgtggaa | 480 |
| catcttgaag | cccctcatca | gtcacaagtt | tgggaagaaa | gtcatctatt | tcaactacct | 540 |
| gagtgagctc | cacgaacacc | ttaaatacga | ccagctggtc | atccctcccg | aagttttgcg | 600 |
| gtacgatgag | aagctccaga | gcctgcacga | gggccggacg | ccgcctccca | ccaagacacc | 660 |
| tccgccgcgg | ccccgctgc | ccacacagca | gtttggcgtc | agtctgcaat | acctcaaaga | 720 |
| caaaaatcaa | ggcgaactca | tcccccctgt | gctgaggttc | acagtgacgt | acctgagaga | 780 |
| gaaaggcctg | cgcaccgagg | gcctgttccg | gagatccgcc | agcgtgcaga | ccgtccgcga | 840 |
| gatccagagg | ctctacaacc | aagggaagcc | cgtgaacttt | gacgactacg | ggacattca | 900 |
| catccctgcc | gtgatcctga | agaccttcct | gcgagagctg | cccagccgc | ttctgacctt | 960 |
| ccaggcctac | gagcagattc | tcgggatcac | ctgtgtggag | agcagcctgc | gtgtcactgg | 1020 |
| ctgccgccag | atcttacgga | gcctcccaga | gcacaactac | gtcgtcctcc | gctacctcat | 1080 |
| gggcttcctg | catgcggtgt | cccgggagag | catcttcaac | aaaatgaaca | gctctaacct | 1140 |
| ggcctgtgtc | ttcgggctga | atttgatctg | gccatcccag | ggggtctcct | ccctgagtgc | 1200 |
| ccttgtgccc | ctgaacatgt | tcactgaact | gctgatcgag | tactatgaaa | agatcttcag | 1260 |
| cacccccggag | gcacctgggg | agcacggcct | ggcaccatgg | gaacaggga | gcagggcagc | 1320 |
| cccctttgcag | gaggctgtgc | cacggacaca | agccacgggc | ctcaccaagc | ctaccctacc | 1380 |
| tccgagtccc | ctgatggcag | ccagaagacg | tctctagtgt | tgcgaacact | ctgtatattt | 1440 |
| cgagctacct | cccacacctg | tctgtgcact | tgtatgtttt | ataaacttgg | catctgtaaa | 1500 |
| ataaccagc | cattagatga | attcagaacc | ttctaatgaa | aaaaaaaa | | 1549 |

<210> SEQ ID NO 29
<211> LENGTH: 1539
<212> TYPE: DNA
<213> ORGANISM: Homo sapiens
<220> FEATURE:
<221> NAME/KEY: misc_feature
<223> OTHER INFORMATION: Incyte ID No: 404424.5

<400> SEQUENCE: 29

| | | | | | |
|---|---|---|---|---|---|
| gcagacccgg | cacgcaggtg | ggggccggcg | gggtccgtgg | accagagctg | cagagagaca | 60 |
| aggcggcggc | ggctgctgtg | ctgggtgcag | tgaggaagag | gccctcggtg | gtgcccatgg | 120 |
| ctggccagga | tcctgcgctg | agcacgagtc | acccgttcta | cgacgtggcc | agacatggca | 180 |
| ttctgcaggt | ggcaggggat | gaccgctttg | gaagacgtgt | tgtcacgttc | agctgctgcc | 240 |
| ggatgccacc | ctcccacgag | ctggaccacc | agcggctgct | ggagtatttg | aagtacacac | 300 |
| tggaccaata | cgttgagaac | gattatacca | tcgtctattt | ccactacggg | ctgaacagcc | 360 |

-continued

```
ggaacaagcc ttccctgggc tggctccaga gcgcatacaa ggagttcgat aggaagtaca      420
agaagaactt gaaggccctc tacgtggtgc accccaccag cttcatcaag gtcctgtgga      480
acatcttgaa gcccctcatc agtcacaagt ttgggaagaa agtcatctat ttcaactacc      540
tgagtgagct ccacgaacac cttaaatacg accagctggt catccctccc gaagttttgc      600
ggtacgatga aagctccag agcctgcacg agggccggac gccgcctccc accaagacac       660
caccgccgcg gcccccgctg cccacacagc agtttggcgt cagtctgcaa tacctcaaag      720
acaaaaatca aggcgaactc atccccctg tgctgaggtt cacagtgacg tacctgagag       780
agaaaggcct gcgcaccgag ggcctgttcc ggagatccgc cagcgtgcag accgtccgcg      840
agatccagag gctctacaac caagggaagc ccgtgaactt tgacgactac ggggacattc      900
acatccctgc cgtgatcctg aagaccttcc tgcgagagct gccccagccg cttctgacct      960
tccaggccta cgagcagatt ctcgggatca cctgtgtgga gagcagcctg cgcgtcactc     1020
gctgccgcca gatcttacgg agcctcccag agcacaacta cgtcgtcctc cgctacctca     1080
tgggcttcct gcatgcggtg tcccgggaga gcatcttcaa caaaatgaac agctctaacc     1140
tggcctgtgt cttcgggctg aatttgatct ggccatccca gggggtctcc tccctgagtg     1200
cccttgtgcc cctgaacatg ttcactgaac tgctgatcga gtactatgaa agatcttca      1260 gcaccccgga ggcacctggg gagcacggcc tggcaccatg ggaacagggg agcagggcag     1320 ccccttttgca ggaggctgtg ccacggacaa agccacggg cctcaccaag cctaccctac      1380
ctccgagtcc cctgatggca gccagaagac gtctctagtg ttgcgaacac tctgtatgtt     1440
tcgagctacc tcccacacct gtctgtgcac ttgtatgttt tgtaaacttg gcatctgtaa     1500
aaataaccag ccattagatg aattcagaac cttctaatg                            1539
```

<210> SEQ ID NO 30
<211> LENGTH: 433
<212> TYPE: PRT
<213> ORGANISM: Homo sapiens
<220> FEATURE:
<221> NAME/KEY: misc_feature
<223> OTHER INFORMATION: Incyte ID No: 3068538CD1

<400> SEQUENCE: 30

```
Met Ala Gly Gln Asp Pro Ala Leu Ser Thr Ser His Pro Phe Tyr
 1               5                  10                  15

Asp Val Ala Arg His Gly Ile Leu Gln Val Ala Gly Asp Asp Arg
                20                  25                  30

Phe Gly Arg Arg Val Val Thr Phe Ser Cys Cys Arg Met Pro Pro
            35                  40                  45

Ser His Glu Leu Asp His Gln Arg Leu Leu Glu Tyr Leu Lys Tyr
        50                  55                  60

Thr Leu Asp Gln Tyr Val Glu Asn Asp Tyr Thr Ile Val Tyr Phe
    65                  70                  75

His Tyr Gly Leu Asn Ser Arg Asn Lys Pro Ser Leu Gly Trp Leu
            80                  85                  90

Gln Ser Ala Tyr Lys Glu Phe Asp Arg Lys Tyr Lys Lys Asn Leu
        95                  100                 105

Lys Ala Leu Tyr Val Val His Pro Thr Ser Phe Ile Lys Val Leu
        110                 115                 120

Trp Asn Ile Leu Lys Pro Leu Ile Ser His Lys Phe Gly Lys Lys
        125                 130                 135

Val Ile Tyr Phe Asn Tyr Leu Ser Glu Leu His Glu His Leu Lys
```

-continued

```
                    140                 145                 150
Tyr Asp Gln Leu Val Ile Pro Pro Glu Val Leu Arg Tyr Asp Glu
                155                 160                 165
Lys Leu Gln Ser Leu His Glu Gly Arg Thr Pro Pro Thr Lys
            170                 175                 180
Thr Pro Pro Arg Pro Pro Leu Pro Thr Gln Gln Phe Gly Val
        185                 190                 195
Ser Leu Gln Tyr Leu Lys Asp Lys Asn Gln Gly Glu Leu Ile Pro
    200                 205                 210
Pro Val Leu Arg Phe Thr Val Thr Tyr Leu Arg Glu Lys Gly Leu
                215                 220                 225
Arg Thr Glu Gly Leu Phe Arg Arg Ser Ala Ser Val Gln Thr Val
                230                 235                 240
Arg Glu Ile Gln Arg Leu Tyr Asn Gln Gly Lys Pro Val Asn Phe
                245                 250                 255
Asp Asp Tyr Gly Asp Ile His Ile Pro Ala Val Ile Leu Lys Thr
                260                 265                 270
Phe Leu Arg Glu Leu Pro Gln Pro Leu Leu Thr Phe Gln Ala Tyr
                275                 280                 285
Glu Gln Ile Leu Gly Ile Thr Cys Val Glu Ser Ser Leu Arg Val
                290                 295                 300
Thr Gly Cys Arg Gln Ile Leu Arg Ser Leu Pro Glu His Asn Tyr
                305                 310                 315
Val Val Leu Arg Tyr Leu Met Gly Phe Leu His Ala Val Ser Arg
                320                 325                 330
Glu Ser Ile Phe Asn Lys Met Asn Ser Ser Asn Leu Ala Cys Val
                335                 340                 345
Phe Gly Leu Asn Leu Ile Trp Pro Ser Gln Gly Val Ser Ser Leu
                350                 355                 360
Ser Ala Leu Val Pro Leu Asn Met Phe Thr Glu Leu Leu Ile Glu
                365                 370                 375
Tyr Tyr Glu Lys Ile Phe Ser Thr Pro Glu Ala Pro Gly Glu His
                380                 385                 390
Gly Leu Ala Pro Trp Glu Gln Gly Ser Arg Ala Ala Pro Leu Gln
                395                 400                 405
Glu Ala Val Pro Arg Thr Gln Ala Thr Gly Leu Thr Lys Pro Thr
                410                 415                 420
Leu Pro Pro Ser Pro Leu Met Ala Ala Arg Arg Leu
                425                 430

<210> SEQ ID NO 31
<211> LENGTH: 433
<212> TYPE: PRT
<213> ORGANISM: Homo sapiens
<220> FEATURE:
<221> NAME/KEY: misc_feature
<223> OTHER INFORMATION: Incyte ID No: 404424.5.pseq

<400> SEQUENCE: 31

Met Ala Gly Gln Asp Pro Ala Leu Ser Thr Ser His Pro Phe Tyr
  1               5                  10                  15
Asp Val Ala Arg His Gly Ile Leu Gln Val Ala Gly Asp Asp Arg
                 20                  25                  30
Phe Gly Arg Arg Val Val Thr Phe Ser Cys Cys Arg Met Pro Pro
                 35                  40                  45
```

-continued

```
Ser His Glu Leu Asp His Gln Arg Leu Glu Tyr Leu Lys Tyr
             50                  55                  60

Thr Leu Asp Gln Tyr Val Glu Asn Asp Tyr Thr Ile Val Tyr Phe
             65                  70                  75

His Tyr Gly Leu Asn Ser Arg Asn Lys Pro Ser Leu Gly Trp Leu
             80                  85                  90

Gln Ser Ala Tyr Lys Glu Phe Asp Arg Lys Tyr Lys Lys Asn Leu
             95                 100                 105

Lys Ala Leu Tyr Val Val His Pro Thr Ser Phe Ile Lys Val Leu
            110                 115                 120

Trp Asn Ile Leu Lys Pro Leu Ile Ser His Lys Phe Gly Lys Lys
            125                 130                 135

Val Ile Tyr Phe Asn Tyr Leu Ser Glu Leu His Glu His Leu Lys
            140                 145                 150

Tyr Asp Gln Leu Val Ile Pro Pro Glu Val Leu Arg Tyr Asp Glu
            155                 160                 165

Lys Leu Gln Ser Leu His Glu Gly Arg Thr Pro Pro Thr Lys
            170                 175                 180

Thr Pro Pro Arg Pro Pro Leu Pro Thr Gln Gln Phe Gly Val
            185                 190                 195

Ser Leu Gln Tyr Leu Lys Asp Lys Asn Gln Gly Glu Leu Ile Pro
            200                 205                 210

Pro Val Leu Arg Phe Thr Val Thr Tyr Leu Arg Glu Lys Gly Leu
            215                 220                 225

Arg Thr Glu Gly Leu Phe Arg Arg Ser Ala Ser Val Gln Thr Val
            230                 235                 240

Arg Glu Ile Gln Arg Leu Tyr Asn Gln Gly Lys Pro Val Asn Phe
            245                 250                 255

Asp Asp Tyr Gly Asp Ile His Ile Pro Ala Val Ile Leu Lys Thr
            260                 265                 270

Phe Leu Arg Glu Leu Pro Gln Pro Leu Leu Thr Phe Gln Ala Tyr
            275                 280                 285

Glu Gln Ile Leu Gly Ile Thr Cys Val Glu Ser Ser Leu Arg Val
            290                 295                 300

Thr Arg Cys Arg Gln Ile Leu Arg Ser Leu Pro Glu His Asn Tyr
            305                 310                 315

Val Val Leu Arg Tyr Leu Met Gly Phe Leu His Ala Val Ser Arg
            320                 325                 330

Glu Ser Ile Phe Asn Lys Met Asn Ser Ser Asn Leu Ala Cys Val
            335                 340                 345

Phe Gly Leu Asn Leu Ile Trp Pro Ser Gln Gly Val Ser Ser Leu
            350                 355                 360

Ser Ala Leu Val Pro Leu Asn Met Phe Thr Glu Leu Leu Ile Glu
            365                 370                 375

Tyr Tyr Glu Lys Ile Phe Ser Thr Pro Glu Ala Pro Gly Glu His
            380                 385                 390

Gly Leu Ala Pro Trp Glu Gln Gly Ser Arg Ala Ala Pro Leu Gln
            395                 400                 405

Glu Ala Val Pro Arg Thr Gln Ala Thr Gly Leu Thr Lys Pro Thr
            410                 415                 420

Leu Pro Pro Ser Pro Leu Met Ala Ala Arg Arg Leu
            425                 430
```

-continued

```
<210> SEQ ID NO 32
<211> LENGTH: 333
<212> TYPE: PRT
<213> ORGANISM: Homo sapiens
<220> FEATURE:
<221> NAME/KEY: misc_feature
<223> OTHER INFORMATION: Incyte ID No: g6572185

<400> SEQUENCE: 32

Tyr Lys Lys Asn Leu Lys Ala Leu Tyr Val His Pro Thr Ser
  1               5                  10                  15

Phe Ile Lys Val Leu Trp Asn Ile Leu Lys Pro Leu Ile Ser His
             20                  25                  30

Lys Phe Gly Lys Val Ile Tyr Phe Asn Tyr Leu Ser Glu Leu
             35                  40                  45

His Glu His Leu Lys Tyr Asp Gln Leu Val Ile Pro Pro Glu Val
             50                  55                  60

Leu Arg Tyr Asp Glu Lys Leu Gln Ser Leu His Glu Gly Arg Thr
             65                  70                  75

Pro Pro Pro Thr Lys Thr Pro Pro Arg Pro Pro Leu Pro Thr
             80                  85                  90

Gln Gln Phe Gly Val Ser Leu Gln Tyr Leu Lys Asp Lys Asn Gln
             95                 100                 105

Gly Glu Leu Ile Pro Pro Val Leu Arg Phe Thr Val Thr Tyr Leu
            110                 115                 120

Arg Glu Lys Gly Leu Arg Thr Glu Gly Leu Phe Arg Arg Ser Ala
            125                 130                 135

Ser Val Gln Thr Val Arg Glu Ile Gln Arg Leu Tyr Asn Gln Gly
            140                 145                 150

Lys Pro Val Asn Phe Asp Asp Tyr Gly Asp Ile His Ile Pro Ala
            155                 160                 165

Val Ile Leu Lys Thr Phe Leu Arg Glu Leu Pro Gln Pro Leu Leu
            170                 175                 180

Thr Phe Gln Ala Tyr Glu Gln Ile Leu Gly Ile Thr Cys Val Glu
            185                 190                 195

Ser Ser Leu Arg Val Thr Gly Cys Arg Gln Ile Leu Arg Ser Leu
            200                 205                 210

Pro Glu His Asn Tyr Val Val Leu Arg Tyr Leu Met Gly Phe Leu
            215                 220                 225

His Ala Val Ser Arg Glu Ser Ile Phe Asn Lys Met Asn Ser Ser
            230                 235                 240

Asn Leu Ala Cys Val Phe Gly Leu Asn Leu Ile Trp Pro Ser Gln
            245                 250                 255

Gly Val Ser Ser Leu Ser Ala Leu Val Pro Leu Asn Met Phe Thr
            260                 265                 270

Glu Leu Leu Ile Glu Tyr Tyr Glu Lys Ile Phe Ser Thr Pro Glu
            275                 280                 285

Ala Pro Gly Glu His Gly Leu Ala Pro Trp Glu Gln Gly Ser Arg
            290                 295                 300

Ala Ala Pro Leu Gln Glu Ala Val Pro Arg Thr Gln Ala Thr Gly
            305                 310                 315

Leu Thr Lys Pro Thr Leu Pro Pro Ser Pro Leu Met Ala Ala Arg
            320                 325                 330

Arg Arg Leu
```

```
<210> SEQ ID NO 33
<211> LENGTH: 439
<212> TYPE: PRT
<213> ORGANISM: Homo sapiens
<220> FEATURE:
<221> NAME/KEY: misc_feature
<223> OTHER INFORMATION: Incyte ID No: g312212

<400> SEQUENCE: 33

Met Asp Pro Leu Ser Glu Leu Gln Asp Asp Leu Thr Leu Asp Asp
 1               5                  10                  15

Thr Ser Glu Ala Leu Asn Gln Leu Lys Leu Ala Ser Ile Asp Glu
                20                  25                  30

Lys Asn Trp Pro Ser Asp Glu Met Pro Asp Phe Pro Lys Ser Asp
                35                  40                  45

Asp Ser Lys Ser Ser Ser Pro Glu Leu Val Thr His Leu Lys Trp
                50                  55                  60

Asp Asp Pro Tyr Tyr Asp Ile Ala Arg His Gln Ile Val Glu Val
                65                  70                  75

Ala Gly Asp Asp Lys Tyr Gly Arg Lys Ile Ile Val Phe Ser Ala
                80                  85                  90

Cys Arg Met Pro Pro Ser His Gln Leu Asp His Ser Lys Leu Leu
                95                 100                 105

Gly Tyr Leu Lys His Thr Leu Asp Gln Tyr Val Glu Ser Asp Tyr
               110                 115                 120

Thr Leu Leu Tyr Leu His His Gly Leu Thr Ser Asp Asn Lys Pro
               125                 130                 135

Ser Leu Ser Trp Leu Arg Asp Ala Tyr Arg Glu Phe Asp Arg Lys
               140                 145                 150

Tyr Lys Lys Asn Ile Lys Ala Leu Tyr Ile Val His Pro Thr Met
               155                 160                 165

Phe Ile Lys Thr Leu Leu Ile Leu Phe Lys Pro Leu Ile Ser Phe
               170                 175                 180

Lys Phe Gly Gln Lys Ile Phe Tyr Val Asn Tyr Leu Ser Glu Leu
               185                 190                 195

Ser Glu His Val Lys Leu Glu Gln Leu Gly Ile Pro Arg Gln Val
               200                 205                 210

Leu Lys Tyr Asp Asp Phe Leu Lys Ser Thr Gln Lys Ser Pro Ala
               215                 220                 225

Thr Ala Pro Lys Pro Met Pro Pro Arg Pro Pro Leu Pro Asn Gln
               230                 235                 240

Gln Phe Gly Val Ser Leu Gln His Leu Gln Glu Lys Asn Pro Glu
               245                 250                 255

Gln Glu Pro Ile Pro Ile Val Leu Arg Glu Thr Val Ala Tyr Leu
               260                 265                 270

Gln Ala His Ala Leu Thr Thr Glu Gly Ile Phe Arg Arg Ser Ala
               275                 280                 285

Asn Thr Gln Val Val Arg Glu Val Gln Gln Lys Tyr Asn Met Gly
               290                 295                 300

Leu Pro Val Asp Phe Asp Gln Tyr Asn Glu Leu His Leu Pro Ala
               305                 310                 315

Val Ile Leu Lys Thr Phe Leu Arg Glu Leu Pro Glu Pro Leu Leu
               320                 325                 330

Thr Phe Asp Leu Tyr Pro His Val Gly Phe Leu Asn Ile Asp
               335                 340                 345
```

-continued

```
Glu Ser Gln Arg Val Pro Ala Thr Leu Gln Val Leu Gln Thr Leu
            350                 355                 360

Pro Glu Glu Asn Tyr Gln Val Leu Arg Phe Leu Thr Ala Phe Leu
            365                 370                 375

Val Gln Ile Ser Ala His Ser Asp Gln Asn Lys Met Thr Asn Thr
            380                 385                 390

Asn Leu Ala Val Val Phe Gly Pro Asn Leu Leu Trp Ala Lys Asp
            395                 400                 405

Ala Ala Ile Thr Leu Lys Ala Ile Asn Pro Ile Asn Thr Phe Thr
            410                 415                 420

Lys Phe Leu Leu Asp His Gln Gly Glu Leu Phe Pro Ser Pro Asp
            425                 430                 435

Pro Ser Gly Leu
```

NUCLEIC ACIDS ENCODING GTPASE ACTIVATING PROTEINS

FIELD OF THE INVENTION

This invention relates to nucleic acid molecules and the encoded GTPase activating proteins, and variants thereof, and to the use of these molecules in the characterization, diagnosis, prevention, and treatment of cell signaling, immune, and cell proliferative disorders, particularly colon cancer.

BACKGROUND OF THE INVENTION

Guanine nucleotide binding proteins (GTP-binding proteins) are present in all eukaryotic cells and function in processes including metabolism, cellular growth, differentiation, signal transduction, cytoskeletal organization, and intracellular vesicle transport and secretion. In higher organisms they are involved in signaling that regulates such processes as the immune response (Aussel et al (1988) J Immunol 140:215–220), apoptosis, differentiation, and cell proliferation including oncogenesis (Dhanasekaran et al. (1998) Oncogene 17:1383–1394).

The superfamily of GTP-binding proteins consists of several families and may be grouped as translational factors, heterotrimeric GTP-binding proteins involved in transmembrane signaling processes (also called G-proteins), proto-oncogene Ras proteins, and other low molecular weight GTP-binding proteins including the products of rab, rap, rho, rac, smg21, smg25, YPT, SEC4, and ARF genes, and tubulins (Kaziro et al. (1991) Ann Rev Biochem 60:349–400).

The low molecular weight (LMW) GTP-binding proteins are a class of small proteins of 21–30 kDa. These proteins regulate cell growth, cell cycle control, protein secretion, and intracellular vesicle interaction. In particular, LMW GTP-binding proteins activate cellular proteins by transducing mitogenic signals involved in various cell functions in response to extracellular signals from receptors (Tavitian (1995) C R Seances Soc Biol Fil 189:7–12). During this process, the hydrolysis of GTP acts as an energy source as well as the means of converting the GTP-binding protein from an active (GTP-bound) to and inactive (GDP-bound) form.

The Rho family of LMW GTP-binding proteins ( Rho GTPases) includes RhoA, Rac 1, and Cdc42 which regulate a variety of biological events related to actin-cytoskeletal reorganization and cell proliferation. A key group of regulatory molecules for the Rho GTPases is the Rho GTPase-activating proteins (GAPs). Rho GAPs preferentially recognize the GTP-bound form of a Rho GTPase and stimulate the intrinsic GTPase activity to hydrolyze the bound GTP to GDP. Rho GAPs therefore function as negative regulators or suppressors of Rho GTPase by stimulating the conversion of the Rho GTPase from the active GTP-bound form to the inactive GDP-bound form (Zhang. et al. (1997) J Biol Chem 272:21999–22007).

Rho GAP proteins share an approximately 170–190 amino acid homology region, designated as the Rho GAP domain, that appears to contain the minimum structural domain necessary for GAP activity (Zheng. et al. (1993) J Biol Chem 24629–24634). Rho GAP proteins share 20–24% amino acid identity in this domain, however, certain specific residues are highly conserved. For example, a pair of arginine residues located near the N-terminus of the Rho GAP domain appear to be highly conserved among Rho GAP proteins and are necessary for maximum catalysis (Leonard et al. (1998) J Biol Chem 273:16210–16215). In addition, a proline-rich, SH3 domain-binding site is also found in the N-terminal region of these proteins (Leonard, supra).

The identification of genes associated with cancer and understanding the genetic mechanisms underlying carcinogenesis are critical to the diagnosis, prevention, and treatment of these diseases. In colon cancer particularly, it is known that a combination of activation of oncogenes, inactivation of tumor suppressor genes, and alteration of DNA mismatch repair genes is involved in the progression from normal mucosa to colon cancer (Fearon et al. (1990) Cell 61:759–767; Chung (1995) Gastroenterology 109:1685–1699). Recently a study was conducted which identified a specific region of chromosome 22 associated with colon cancer based on chromosomal (gene?) allelic losses in colon tumor samples relative to normal colon mucosa (Castells et al. (1999) Gastroenterology 117:8331–837). Using microsatellite markers from chromosome 22, a minimal region of allelic deletion was identified between markers D22S1171 and D22S928 covering an interval of 0.57 cM and corresponding to the cytogenetic location 22q13.33. Various genes on chromosome 22 have been proposed as candidate tumor-suppressor genes associated with colorectal carcinogenesis, however, no mutations have been found in any of these genes (Castells et al. supra).

The discovery of nucleic acid sequences encoding GTPase-activating proteins and variants thereof provides new compositions that are useful in the characterization, diagnosis, prevention, and treatment of cell proliferative disorders, including cancer and, in particular, colon cancer.

SUMMARY OF THE INVENTION

The invention is based on the discovery of nucleic acid molecules encoding GTPase-activating protein referred to collectively as "GTPAP" and individually as "GTPAP1 and GTPAP2" and variants thereof, which satisfies a need in the art by providing compositions useful in the characterization, diagnosis, prevention, and treatment of conditions such as cell signaling, immune, and cell proliferative disorders, particularly colon cancer.

The invention provides isolated and purified human and rat nucleic acid molecules comprising SEQ ID NOs:1–29, and fragments thereof, encoding the mammalian protein comprising the amino acid sequence of SEQ ID NO:30, or portions thereof, a biologically active portion of SEQ ID NO:30, an immunologically active portion of SEQ ID NO:30, and a variant of SEQ ID NO:30 comprising SEQ ID NO:31.

The invention further provides a probe that hybridizes to the mammalian nucleic acid molecules or fragments thereof. The invention also provides isolated and purified nucleic acid molecules that are complementary to the nucleic acid molecules of SEQ ID NOs:1–29. In one aspect, the probe is a single stranded complementary RNA or DNA molecule.

The invention further provides a method for detecting a nucleic acid molecule in a sample, the method comprising the steps of hybridizing a probe to at least one nucleic acid molecule of a sample, forming a hybridization complex; and detecting the hybridization complex, wherein the presence of the hybridization complex indicates the presence of the nucleic acid molecule in the sample. In one aspect, the method further comprises amplifying the nucleic acid molecule prior to hybridization. The nucleic acid molecule or a fragment thereof may comprise either an element or a target on a microarray.

The invention also provides a method for using a nucleic acid molecule or a fragment thereof to screen a library of molecules to identify at least one ligand that specifically binds the nucleic acid molecule, the method comprising combining the nucleic acid molecule with a library of molecules under conditions allowing specific binding, and detecting specific binding, thereby identifying a ligand that specifically binds the nucleic acid molecule. Such libraries include DNA and RNA molecules, peptides, PNAs, proteins, and the like. In an analogous method, the nucleic acid molecule or a fragment thereof is used to purify a ligand.

The invention also provides an expression vector containing at least a fragment of the nucleic acid molecule. In another aspect, the expression vector is contained within a host cell. The invention further provides a method for producing a protein, the method comprising the steps of culturing the host cell under conditions for the expression of the protein and recovering the protein from the host cell culture.

The invention also provides substantially purified mammalian GTPAP or a portion thereof. The invention further provides isolated and purified proteins having the amino acid sequence of SEQ ID NO:30, a biologically active portion of SEQ ID NO:30, and an immunologically active portion of SEQ ID NO:30, and a variant of SEQ ID NO:30 comprising SEQ ID NO:31. Additionally, the invention provides a pharmaceutical composition comprising a substantially purified mammalian GTPAP protein or a portion thereof in conjunction with a pharmaceutical carrier.

The invention also provides a method for treating a disease or condition associated with altered expression of GTPAP, comprising administering to a patient in need of such treatment an effective amount of a pharmaceutical composition comprising a substantially purified mammalian GTPAP protein or a portion thereof in conjunction with a pharmaceutical carrier. In one embodiment of the invention, the disease or condition is selected from cell signaling, immune, and cell proliferative disorders, particularly colon cancer. In another embodiment of the invention, the cancer is a colon cancer.

The invention further provides a method for using at least a portion of the mammalian protein to produce antibodies. The invention also provides a method for using a mammalian protein or a portion thereof to screen a library of molecules to identify at least one ligand that specifically binds the protein, the method comprising combining the protein with the library of molecules under conditions allowing specific binding, and detecting specific binding, thereby identifying a ligand that specifically binds the protein. Such libraries include DNA and RNA molecules, peptides, agonists, antagonists, antibodies, immunoglobulins, drug compounds, pharmaceutical agents, and other ligands. In one aspect, the ligand identified using the method modulates the activity of the mammalian protein. In an analogous method, the protein or a portion thereof is used to purify a ligand. The method involves combining the mammalian protein or a portion thereof with a sample under conditions to allow specific binding, detecting specific binding between the protein and ligand, recovering the bound protein, and separating the protein from the ligand to obtain purified ligand.

The invention further provides a method for inserting a marker gene into the genomic DNA of a mammal to disrupt the expression of the natural mammalian nucleic acid molecule. The invention also provides a method for using the mammalian nucleic acid molecule to produce a mammalian model system, the method comprising constructing a vector containing the mammalian nucleic acid molecule; introducing the vector into a totipotent mammalian embryonic stem cell; selecting an embryonic stem cell with the vector integrated into genomic DNA; microinjecting the selected cell into a mammalian blastocyst, thereby forming a chimeric blastocyst; transferring the chimeric blastocyst into a pseudopregnant dam, wherein the dam gives birth to a chimeric mammal containing at least one additional copy of mammalian nucleic acid molecule in its germ line; and breeding the chimeric mammal to generate a homozygous mammalian model system.

BRIEF DESCRIPTION OF THE FIGURES AND TABLE

Table 1 shows the tools, programs, and algorithms used to analyze GTPAP, along with applicable descriptions, references, and threshold parameters.

FIGS. 1A, 1B, 1C, 1D, and 1E show the human nucleic acid molecule (SEQ ID NO:28) encoding the human amino acid sequence (SEQ ID NO:30) of the mammalian protein. The alignment was produced using MACDNASIS PRO software (Hitachi Software Engineering, South San Francisco Calif.).

FIGS. 2A, 2B, 2C, 2D, and 2E show the human nucleic acid molecule (SEQ ID NO:29) encoding the human amino acid sequence (SEQ ID NO:31) of the mammalian protein. The alignment was produced using MACDNASIS PRO software (Hitachi Software Engineering)

Figure 3B:
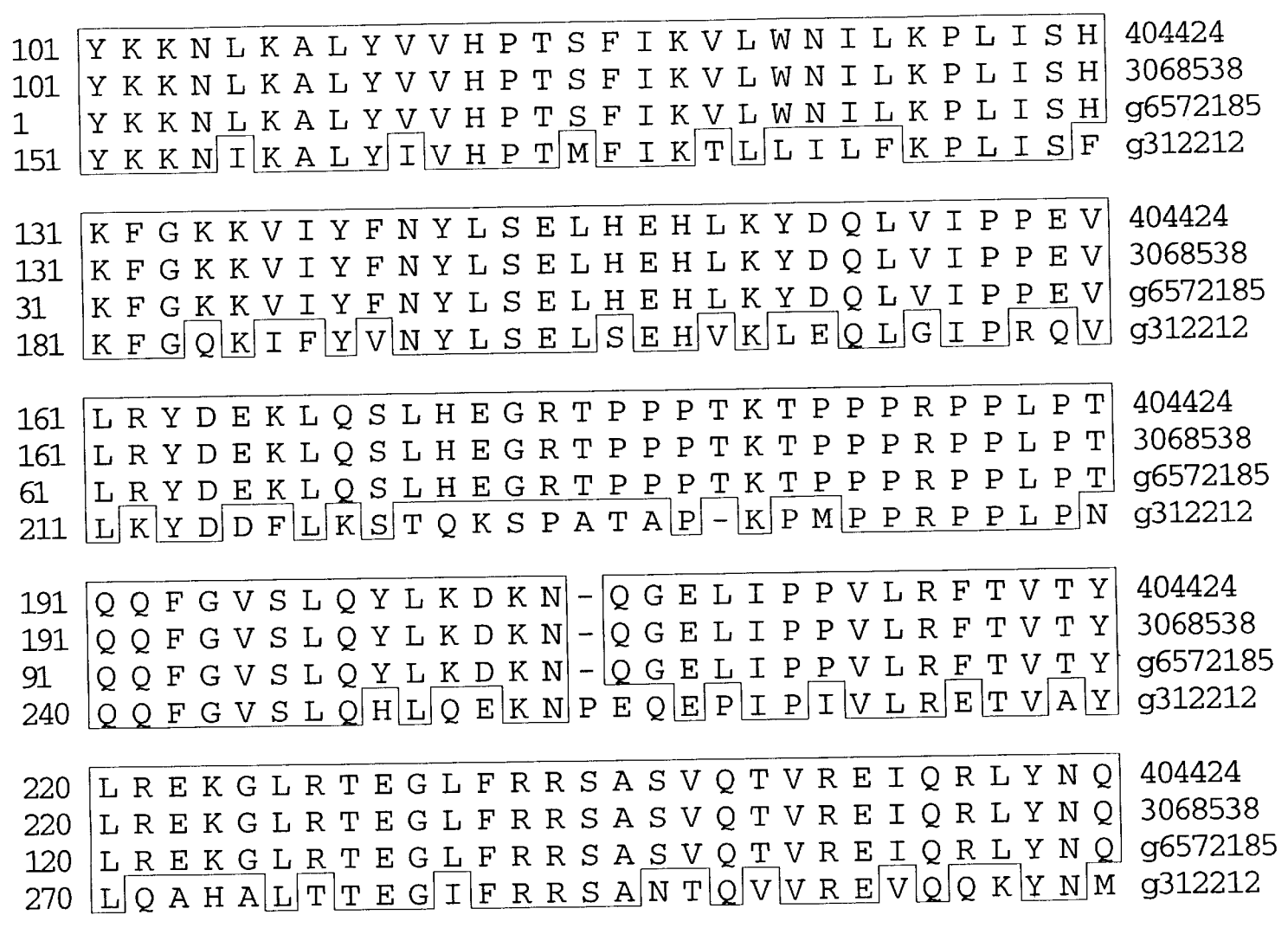

FIGS. 3A, 3B, 3C, and 3D demonstrate the chemical and structural similarity among human RhoGAP proteins, GTPAP2 (clone ID 404424;SEQ ID NO:31), GTPAP1 (clone ID 3068538;SEQ ID NO:30), Rho GTPase activating protein 8 (GI 6572185;SEQ ID NO:32), and rhoGAP protein (GI 312212;SEQ ID NO:33). The alignments were produced using the MEGALIGN program (DNASTAR, Madison Wis.)

FIGS. 4A and 4B demonstrate the alignments among nucleic acids encoding human GTPAP and indicating regions of single nucleotide polymorphisms (SNPs). SNPs are indicated by (Δ). The alignments were produced using PHRAP software (Phil Green, University of Washington, Seattle Wash).

FIGS. 5A, 5B, 5C, 5D, and 5E demonstrate the chemical and structural similarity among human, 3068538CB1 (SEQ ID NO:28); and rat, 701244926H1 (SEQ ID NO:21), 700950169H2 (SEQ ID NO:22), 70157597H1 (SEQ ID NO:23), 701274036H1 (SEQ ID NO:24), 700480528 (SEQ ID NO:25), 700935753H1 (SEQ ID NO:26), and 700936061H1 (SEQ ID NO:27) nucleic acid sequences, produced using PHRAP software (Phil Green, University of Washington, Seattle Wash.).

DESCRIPTION OF THE INVENTION

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular forms "a," "an," and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"GTPase-activating protein" or "GTPAP", refers to a substantially purified protein obtained from any mammalian species, including murine, bovine, ovine, porcine, rodent, canine, simian, and preferably the human species, and from any source, whether natural, synthetic, semi-synthetic, or recombinant. "GTPAPs" refers to more than one GTPAP.

"Altered gene expression" and "altered expression" refers to the increase or decrease of gene expression and the presence or absence of transcribed messenger RNA transcribed in a sample.

"Biologically active" refers to a protein having structural, immunological, regulatory, or chemical functions of a naturally occurring, recombinant or synthetic molecule. Likewise, "immunologically active" refers to the capability of the natural, recombinant, or synthetic GTPAP, or of any oligopeptide thereof, to induce a specific immune response in appropriate animals or cells and to bind with specific antibodies.

"Complementary" refer to the natural hydrogen bonding by base pairing between purines and pyrimidines. For example, the sequence A-C-G-T forms hydrogen bonds with its complements T-G-C-A or U-G-C-A. Two single-stranded molecules may be considered partially complementary, if only some of the nucleotides bond, or completely complementary, if nearly all of the nucleotides bond. The degree of complementarity between nucleic acid strands affects the efficiency and strength of the hybridization and amplification reactions.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

"Fragment" refers to an Incyte clone or any part of a nucleic acid molecule that retains a usable, functional characteristic. Useful fragments include oligonucleotides which may be used in hybridization or amplification technologies or in regulation of replication, transcription or translation.

"Hybridization complex" refers to a complex between two nucleic acid molecules by virtue of the formation of hydrogen bonds between purines and pyrimidines.

"Ligand" refers to any molecule, agent, or compound that will bind specifically to a complementary site on a nucleic acid molecule or protein. Such ligands stabilize or modulate the activity of nucleic acid molecules or proteins of the invention and may be composed of at least one of the following: inorganic and organic substances including nucleic acids, proteins, carbohydrates, fats, and lipids.

"Modulates" refers to a change in activity (biological, chemical, or immunological) or lifespan resulting from specific binding between a molecule and either a nucleic acid molecule or a protein.

"Non-conservative amino acid substitutions" are those substitutions that, when made, are most likely to effect the properties of the original protein, i.e., the structure and especially the function of the protein. For example, the substitution of an acidic or basic amino acid, such as aspartate or arginine, for a neutral amino acid, such as glycine or alanine represents a non-conservative substitution. Like wise, "conservative amino acid substitutions" are those substitutions that, when made, least interfere with the properties of the original protein, i.e., the structure and especially the function of the protein is conserved and not significantly changed by such substitutions. The substitution of one neutral amino acid for another, such as valine for alanine is a conservative substitution, as well as the substitution of one acid amino acid for another, such as aspartate for glutamate.

"Non-conservative nucleic acid substitution" refers to the substitution of a pyrimidine nucleotide for a purine nucleotide in a nucleic acid molecule. Likewise a "conservative nucleic acid substitution" refers to the substitution of one pyrimidine or one purine nucleotide for another, such as C for T or A for G.

"Nucleic acid molecule" refers to a nucleic acid, oligonucleotide, nucleotide, polynucleotide or any fragment thereof. It may be DNA or RNA of genomic or synthetic origin, double-stranded or single-stranded, and combined with carbohydrate, lipids, protein or other materials to perform a particular activity such as transformation or form a useful composition such as a peptide nucleic acid (PNA). "Oligonucleotide" is substantially equivalent to the terms amplimer, primer, oligomer, element, target, and probe and is preferably single stranded. The nucleic acid molecules may be splice variants of another nucleic acid molecule.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules that specifically bind to that portion, or for the production of antibodies.

"Similarity" as applied to polynucleotide sequences, refers to the quantified residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

A suite of commonly used and freely available sequence comparison algorithms is provided by the National Center for Biotechnology Information (NCBI), Bethesda Md. BLAST, Basic Local Alignment Search Tool (Altschul et al. (1990) J. Mol. Biol. 215:403–410; Altschul (1993) J. Mol. Evol. 36:290–300), is available from NCBI (.ncbi.nlm.nih.gov/BLAST/) and several other sources. The BLAST software suite includes various sequence analysis programs including "blastn", that is used to align a known polynucleotide sequence with other polynucleotide sequences from a variety of databases. Also available is a tool called "BLAST 2 sequences" that is used for direct pairwise comparison of two nucleotide sequences. "BLAST 2 sequences" can be accessed and used interactively at .ncbi.nlm.nih.gov/gorf/bl2.html. The "BLAST 2 sequences" tool can be used for both blastn and blastp. BLAST programs are commonly used with gap and other parameters set to default settings. For example, to compare two nucleotide sequences, one may use blastn with the "BLAST 2 Sequences" tool Version 2.0.9 (May 7, 1999) set at default parameters. Such default parameters may be, for example: Matrix: BLOSUM62; Reward for match: 1; Penalty for mismatch: -2; Open Gap: 5 and Extension Gap: 2 penalties; Gap x drop-off: 50; Expect: 10; Word Size:. 11; and Filter: on.

Similarity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

"Sample" is used herein in its broadest sense. A sample containing polynucleotides, polypeptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA in solution or bound to a substrate; a cell; a tissue; a tissue print; a fingerprint, skin or hair; and the like.

"Specific binding" or "specifically binding" refers to the interaction between two molecules. In the case of a polynucleotide, specific binding may involve hydrogen bonding between sense and antisense strands or between one stand and a protein which affects its replication or transcription, intercalation of a molecule or compound into the major or minor groove of the DNA molecule, or interaction with at least one molecule which functions as a transcription factor, enhancer, repressor, and the like. In the case of a polypeptide, specific binding may involve interactions with polynucleotides, as described above or with molecules or compounds such as agonists, antibodies, antagonists, and the like. Specific binding is dependent upon the presence of structural features that allow appropriate chemical or molecular interactions between molecules.

"Single Nucleotide Polymorphism", or SNP, refers to a single nucleotide alteration in a polynucleotide that occurs as a result of a substitution, insertion or deletion. The substitution may be conservative or non-conservative, as defined above, and may or may not result in a change in an encoded amino acid residue. Such changes may predispose an individual to a specific disease or condition.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to nucleic acid molecules that are variants of a nucleic acid molecule that encodes GTPAP, or to the proteins encoded by these molecules. Such variants may be determined by BLAST score, wherein the score is at least 100, and most preferably at least 400.

The Invention

The invention is based on the discovery of new mammalian nucleic acid molecules that encode GTPAPs and nucleic acid molecule variants thereof, and on the use of the nucleic acid molecules, or fragments thereof, and protein, or portions thereof, as compositions in the characterization, diagnosis, treatment, or prevention of conditions such as cell signaling, immune, and cell proliferative disorders, particularly colon cancer.

Nucleic acids encoding GTPAP1 of the present invention were first identified in Incyte Clone 3068538H1 from the uterine tissue library UTRSNOR01 using a computer search for amino acid sequence alignments. A consensus sequence, SEQ ID NO:28, was derived from Incyte Clones 908465R2;SEQ ID NO:1 (COLNNOT09), 957130R6;SEQ ID NO:2 (KIDNNOT05), 1580628H1;SEQ ID NO:3 (DUODNOT01), 2631247F6;SEQ ID NO:4 (COLNTUT15), 3068538H1;SEQ ID NO:5 (UTRSNOR01), 3532286T6;SEQ ID NO:6 (KIDNNOT25), and 1301520F6;SEQ ID NO:7.

Nucleic acid molecules encoding the human GTPase-activating protein and nucleic acid molecule variants of the present invention were identified by comparing nucleic acid sequences encoding GTPAP1 and GTPAP2 of the present invention with nucleic acid sequences in the LIFESEQ and ZOOSEQ databases (Incyte Pharmaceuticals, Palo Alto Calif.).

In one embodiment, the invention encompasses a polypeptide comprising the amino acid sequence of SEQ ID NO:30, as shown in FIGS. 1A, 1B, 1C, 1D, and 1E. GTPAP1 is 433 amino acids in length and has a potential N-linked glycosylation site at N338. Potential protein kinase phosphorylation sites are found for casein kinse II at S169, T239, T292, S309, and S382, for protein kinase Cat S129, T239, and S297, and for tyrosine kinase at Y60, Y101, and Y315. BLIMPS_PFAM analysis identified an RHG5 GTPase-activator protein signature from amino acid residues D260 through P276. BLIMPS_PRODOM identified two protein GTPase-activator domains from P210 through A235 and from L310 through L350. BLAST_PRODOM analysis also identified homology to an RHG5 RhoGAP protein from L8 through S169 with a probability score of $p=4.3^{-60}$, and to a P50-RhoGAP from T175 through P387 with a probability score of $p=7.9^{-29}$.

In another embodiment, the invention encompasses a polypeptide comprising the amino acid sequence of SEQ ID NO:31, as shown in 2A, 2B, 2C, 2D, and 2E. GTPAP2 is also 433 amino acids in length and shares the same glycosylation sites, phosphorylation sites, motifs and signature sequences as GTPAP1.

As shown in FIGS. 3A, 3B, 3C, and 3D, GTPAP1 shares sequence homology with GTPAP2 (Incyte ID 404424.5;SEQ ID NO:31), a partial amino acid sequence of human RhoGAP protein 8 (GI 6572185:SEQ ID NO:32), and human RhoGAP protein GI 312212 (SEQ ID NO:33). In particular, GTPAP1 and GTPAP2 share 99.8% identity, differing in only one amino acid residue at position 302 in which an arginine residue in GTPAP2 is substituted for a glycine residue at that position in GTPAP1. This substitution results from a SNP in the codon for the amino acid at that position (see polynucleotide alignments in FIGS. 4A and 4B described below). GTPAP1 is identical to GI 6572185 from residues Y101 through L433 of GTPAP1, however GTPAP1 contains an additional 100 amino acid residues on the N-terminus of the protein. GTPAP1 also shares 49.2% identity with GI 312212. The four proteins share a proline-rich region from about amino acid residue P176 through P189 of GTPAP1, the SH3 domain-binding site. The four proteins also share substantial homology in the C-terminal region containing the Rho GAP domain. In particular, the two arginine residues associated with the catalytic activity in GAP proteins contained in the sequence F231RRS of GTPAP1, are conserved in all four proteins. It is also noteworthy that the single amino acid change at position 302 between GTPAP1 (glycine) and GTPAP2 (arginine) is a non-conservative change that occurs in the Rho GAP domain of the protein.

FIGS. 4A and 4B show the alignments between the polynucleotides encoding GTPAP1 (3068538:SEQ ID NO:28) and GTPAP2 (404424.5:SEQ ID NO:29), and Incyte cDNA clones from which these sequences were derived. In particular, the alignments encompass regions in which single nucleotide polymorphism (SNP) changes are found between the two full length polynucleotides. These SNPs are identified by (A) in FIGS. 4A and 4B. The cDNA clones encompassing these regions (and their associated libraries) are; 908465R2; SEQ ID NO 1 (COLNNOT09), 957130R6; SEQ ID NO:2 (KIDNNOT05), 1580628H1; SEQ ID NO:3 (DUODNOT01), 2631247F6; SEQ ID NO:4 (COLNTUT15), 1301520F6; SEQ ID NO:7 (BRSTNOT07), 2465422F6; SEQ ID NO:8 (THYRNOT08), 957130X313V1; SEQ ID NO:9 (KIDNNOT05), 1580545H1; SEQ ID NO:10 (DUODNOT01), 1891457H1; SEQ ID NO:11 (BLADTUT07), 4649657H1; SEQ ID NO:12 (PROSTUT04), 4002758H1; SEQ ID NO:13 (HNT2AZS07), 957130R1; SEQ ID NO:14 (KIDNNOT05), 2624365T6.comp; SEQ ID NO:15 (KERANOT02), 2044444H1; SEQ ID NO16 (HIPONON02), 3416883T6; SEQ ID NO17 (PTHYNOT04), 1301520T6.comp; SEQ ID NO18 (BRSTNOT07), 1301520H1; SEQ ID NO:19 (BRSTNOT07), and 1422635X305D1.comp; SEQ ID NO:20 (KIDNNOT09). FIG. 4A demonstrates a SNP at nucleotide position 661 showing a non-conservative change from T to A in GTPAP2(404424.5) relative to GTAP1 (3068538CB1). This change is supported by 2 of 6 clones containing T in this position, and 4 of 6 clones containing A in this position. FIG. 4B demonstrates SNPs at positions 1012 and 1019. The SNP at position 1012 shows a conservative change of T to C in GTPAP2 and is supported by 2 of 12 clones containing a C in this position compared with 10 of 12 clones containing a T in this position. The SNP at position 1019 shows a non-conservative change of G to C in GTPAP2 and is also supported by 2 of 12 clones containing a C in this position compared with 7 of 12 clones containing G in this position. The SNPs at positions 1012 and 1019 are particularly significant because they are relatively rare, being found in only 2/12 or 17% of the identifiable clones encompassing this region, and because the SNP at position 1019 occurs in the 5' position of the codon for an encoded amino acid residue, resulting in a non-conservative change from glycine to arginine in GTPAP2. The change at position 1019 has potential consequences on the catalytic activity of the encoded protein which is located in this region of the protein.

Additional nucleic acid molecules encoding the mammalian GAP protein of the present invention were identified by using BLAST or BLAST2 (Altschul et al. (1997) Nucleic Acids Res. 25:3389–3402) against the ZOOSEQ database (Incyte Pharmaceuticals, Palo Alto Calif.) to align rat, mouse, and monkey clones with the human Rho GAP protein encoding nucleic acid molecules (SEQ ID NO:28 and SEQ ID NO:29). FIGS. 5A, 5B, 5C, 5D, and 5E show the alignments between SEQ ID NO:28 and non-human variants of this sequence from rat. The following clones, SEQ ID NOs:, (and their libraries) were identified by a BLAST score of at least 100 relative to the human sequence, SEQ ID NO:28: 701244926H1; SEQ ID NO:21 (RALINOH02), 700950169H2; SEQ ID NO:22 (RASPNON02), 701575974H1; SEQ ID NO:23 (RALITXT25), 701274036H1; SEQ ID NO:24 (RABFNON02), 700480528H1; SEQ ID NO:25 (RALINON03), 700935753H1; SEQ ID NO:26 (RALINON03), and 700936061H1; SEQ ID NO:27 (RALINON03).

The nucleic acid sequences, SEQ ID NOs:1–29 may be used in hybridization and amplification technologies to identify and distinguish among SEQ ID NOs:28 and 29 and similar molecules in a sample. The molecules may be used to mimic human conditions, diseases, or disorders, produce transgenic animal models for these conditions, or to monitor animal toxicology studies, clinical trials, and subject/patient treatment profiles.

Northern analysis shows the expression of GTPAP in various tissues, at least 68% of which are associated with cancer, 32% of which are associated with inflammation and the immune response, and 18% of which are associated with cell proliferative conditions. Of particular note is the expression of GTPAP in gastrointestinal tissues (23%) including colon cancer.

Polynucleotides encoding GTPAP were mapped to a region of chromosome 22 containing genes associated with colon cancer. Using the public domain sequence tagged sites D22S1171 and DD22S92 previously found to define a region of chromosome 22 associated with colon cancer, polynucleotide sequences encoding GTPAP were aligned by BLAST2 analysis with genomic DNA within this region and matches found containing a minimum of 98% identity over at least 100 base pairs.

The DNA human sequence encoding the partial amino acid sequence for Rho GAP protein GI 6572185 was recently discovered to be localized to the region of chromosome 22 containing genes associated with colon cancer. Rho GAP proteins are potential tumor suppressors by virtue of their role as negative regulators or suppressors of Rho GTPase modulated signaling processes in normal cells.

Characterization and Use of the Invention cDNA Libraries

In a particular embodiment disclosed herein, mRNA was isolated from mammalian cells and tissues using methods that are well known to those skilled in the art and used to prepare the cDNA libraries. The Incyte clones listed above were isolated from mammalian cDNA libraries. At least one library preparation representative of the invention is described in the EXAMPLES below. The consensus mammalian sequences were chemically and/or electronically assembled from fragments including Incyte clones and extension and/or shotgun sequences using computer programs such as PHRAP (Green, supra), GELVIEW Fragment Assembly system (Genetics Computer Group, Madison Wis.), and AUTOASSEMBLER application (PE Biosystems, Foster City Calif.). Clones, extension and/or shotgun sequences are electronically assembled into clusters and/or master clusters.

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the HYDRA microdispenser (Robbins Scientific, Sunnyvale Calif.), MICROLAB 2200 system (Hamilton, Reno Nev.), and the DNA ENGINE thermal cycler (PTC200; MJ Research, Watertown Mass.). Machines used for sequencing include the ABI PRISM 3700, 377 or 373 DNA sequencing systems (PE Biosystems), the MEGABACE 1000 DNA sequencing system (Amersham Pharmacia Biotech), and the like. The sequences may be analyzed using a variety of algorithms which are well known in the art and described in Ausubel et al. (1997; *Short Protocols in Molecular Biology*, John Wiley & Sons, New York N.Y., unit 7.7) and Meyers (1995; *Molecular Biology and Biotechnology*, Wiley V C H, New York N.Y., pp. 856–853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative regions flanking the nucleic acid molecules of interest. Incomplete assembled sequences are inspected for identity using various algorithms or programs such as CONSED (Gordon (1998) Genome Res. 8:195–202) which are well known in the art. Contaminating sequences including vector or chimeric sequences or deleted sequences can be removed or restored, respectively, organizing the incomplete assembled sequences into finished sequences.

Extension of a Nucleic Acid Sequence

The sequences of the invention may be extended using various PCR-based methods known in the art. For example, the XL-PCR kit (PE Biosystems), nested primers, and commercially available cDNA or genomic DNA libraries may be used to extend the nucleic acid sequence. For all PCR-based methods, primers may be designed using commercially available software, such as OLIGO 4.06 primer analysis software (National Biosciences, Plymouth Minn.) to be about 22 to 30 nucleotides in length, to have a GC content of about 50% or more, and to anneal to a target molecule at temperatures from about 55° C. to about 68° C. When extending a sequence to recover regulatory elements, it is preferable to use genomic, rather than cDNA libraries.

Use of the Mammalian Nucleic Acid Nolecule

Hybridization

The mammalian nucleic acid molecule and fragments thereof can be used in hybridization technologies for various purposes. A probe may be designed or derived from unique regions such as the 5' regulatory region or from a conserved motif such as the GTPase-activating protein signature and used in protocols to identify naturally occurring molecules encoding the mammalian protein, allelic variants, or related molecules. The probe may be DNA or RNA, is usually single stranded and should have at least 50% sequence identity to any of the nucleic acid sequences. The probe may comprise at least 16 contiguous nucleotides of a nucleic acid molecule. Hybridization probes may be produced using oligolabeling, nick translation, end-labeling, or PCR amplification in the presence of labeled nucleotide. A vector containing the nucleic acid molecule or a fragment thereof may be used to produce an mRNA probe in vitro by addition of an RNA polymerase and labeled nucleotides. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleic acid sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid molecules are completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or Triton X-100 (Sigma Aldrich, St. Louis Mo.) and a blocking agent such as denatured salmon sperm DNA. Selection of components and conditions for hybridization are well known to those skilled in the art and are reviewed in Ausubel (supra) and Sambrook et al. (1989) *Molecular Cloning. A Laboratoty Manual*, Cold Spring Harbor Press, Plainview N.Y.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natl. Acad. Sci. 93:10614–10619; Baldeschweiler et al. (1995) PCT application WO951251116; Shalon et al. (1995) PCT application WO95/35505; Heller et al. (1997) Proc. Natl. Acad. Sci. 94:2150–2155; and Heller et al. (1997) U.S. Pat. No. 5,605, 662.)

Hybridization probes are also useful in mapping the naturally occurring genomic sequence. The probes may be hybridized to: 1) a particular chromosome, 2) a specific region of a chromosome, 3) artificial chromosome constructions such as human artificial chromosomes (HAC), yeast artificial chromosomes (YAC), bacterial artificial chromosomes (BAC), bacterial P1 constructions, or single chromosomes, or cDNA libraries made from any of these sources.

Expression

A multitude of nucleic acid molecules encoding GTPAP may be cloned into a vector and used to express the protein, or portions thereof, in host cells. The nucleic acid sequence can be engineered by such methods as DNA shuffling (Stemmer and Crameri (1996) U.S. Pat. No. 5,830,721) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources that have been selected for their efficiency in a particular host. The vector, nucleic acid molecule, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells that successfully express the introduced sequences. Resistant clones identified either by survival on selective media or by the expression of visible markers, such as anthocyanins, green fluorescent protein (GFP), β glucuronidase, luciferase, and the like, may be propagated using culture techniques. Visible markers are also used to quantify the amount of protein expressed by the introduced genes. Verification that the host cell contains the desired mammalian nucleic acid molecule is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing that cleaves a "prepro" form may also be used to specify protein targeting, folding, and/or activity. Different host cells available from the ATCC (Manassas Md.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), calmodulin binding peptide (CBP), 6-His, FLAG, MYC, and the like. GST, CBP, and 6-His are purified using commercially available affinity matrices such as immobilized glutathione, calmodulin, and metal-chelate resins, respectively. FLAG and MYC are purified using commercially available monoclonal and polyclonal antibodies. A proteolytic cleavage site may be located between the desired protein sequence and the heterologous moiety for ease of separation following purification. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/ or N, N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1–S20). Automated synthesis may also be carried out on machines such as the ABI 431A peptide synthesizer (PE Biosystems). A protein or portion thereof may be substantially purified by preparative high performance liquid chromatography and its composition confirmed by amino acid analysis or by sequencing (Creighton (1984) *Proteins, Structures and Molecular Properties*, W H Freeman, New York N.Y.).

Preparation and Screening of Antibodies

Various hosts including goats, rabbits, rats, mice, humans, and others may be immunized by injection with GTPAP or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce the chimeric molecule.

Monoclonal antibodies may be prepared using any technique that provides for the production of antibodies by continuous cell lines in culture. These include, but are not limited to, the hybridoma technique, the human B-cell hybridoma technique, and the EBV-hybridoma technique. (See, e.g., Kohler et at. (1975) Nature 256:495–497; Kozbor et al. (1985) J. Immunol. Methods 81:31–42; Cote et al. (1983) Proc. Natl. Acad. Sci. 80:2026–2030; and Cole et al. (1984) Mol. Cell. Biol. 62:109–120.)

Alternatively, techniques described for the production of single chain antibodies may be adapted, using methods known in the art, to produce epitope specific single chain antibodies. Antibody fragments which contain specific binding sites for epitopes of the mammalian protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 246:1275–1281).

The mammalian protein or a portion thereof may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of labels and conjugation techniques are known by those skilled in the art and may be used in various nucleic acid, amino acid, and antibody assays. Synthesis of labeled molecules may be achieved using Promega (Madison Wis.) or Amersham Pharmacia Biotech kits for incorporation of a labeled nucleotide such as $^{32}$P-dCTP, Cy3-dCTP or Cy5-dCTP or amino acid such as $^{35}$S-methionine. Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Diagnostics

The nucleic acid molecules, fragments, oligonucleotides, complementary RNA and DNA molecules, and PNAs may be used to detect and quantify altered gene expression, absence/presence vs. excess, expression of mRNAs or to monitor mRNA levels during therapeutic intervention. Conditions, diseases or disorders associated with altered expression include a cell proliferative disorder such as actinic keratosis, arteriosclerosis, atherosclerosis; bursitis, cirrhosis, hepatitis, mixed connective tissue disease (MCTD), psoriasis, primary thrombocythemia, and cancers including adenocarcinoma, leukemia, lymphoma, melanoma, myeloma, sarcoma, teratocarcinoma, and, in particular, cancer of the colon; an immune disorder such as inflammation, actinic keratosis, acquired immunodeficiency syndrome (AIDS), Addison's disease, adult respiratory distress syndrome, allergies, anemia, asthma, autoimmune thyroiditis, bronchitis, bursitis, cholecystitis, cirrhosis, contact dermatitis, Crohn's disease, diabetes mellitus, emphysema, gout, Graves' disease, hepatitis, hypereosinophilia, irritable bowel syndrome, multiple sclerosis, myasthenia gravis, myocardial or pericardial inflammation, osteoarthritis, osteoporosis, pancreatitis, rheumatoid arthritis, scleroderma, and ulcerative colitis; and a cell signaling disorder including endocrine disorders such as disorders of the hypothalamus and pituitary resulting from lesions such as primary brain tumors, adenomas, hypophysectomy, aneurysms, vascular malformations, thrombosis, and complications due to head trauma; disorders associated with hyperpituitarism including acromegaly, giantism, and syndrome of inappropriate antidiuretic hormone (ADH) secretion (SIADH); disorders associated with hypothyroidism including goiter, myxedema, acute thyroiditis associated with bacterial infection; and disorders associated with hyperparathyroidism including Conn disease (chronic hypercalemia). The diagnostic assay may use hybridization or amplification technology to compare gene expression in a biological sample from a patient to standard samples in order to detect altered gene expression. Qualitative or quantitative methods for this comparison are well known in the art.

For example, the nucleic acid molecule or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed (Coligan et al. (1997) *Current Protocols in Immunology*, Wiley-Interscience, New York N.Y.; Pound, supra).

Therapeutics

Chemical and structural similarity, e.g., in the context of sequences and motifs, exists between regions of GTPAP and GAP proteins. In addition, the expression of GTPAP is closely associated with cell proliferation, particularly colon cancer, and with inflammation and the immune response. Therefore, GTPAP appears to play a role in cell signaling, immune, and cell proliferative disorders, particularly colon cancer. In the treatment of conditions associated with increased expression or activity, it is desirable to decrease expression or protein activity. In the treatment of conditions associated with decreased expression or activity, it is desirable to increase expression or protein activity.

In one embodiment, the mammalian protein or a portion or derivative thereof may be administered to a subject to treat or prevent a condition associated with altered expression or activity of the mammalian protein. Examples of such conditions include, but are not limited to, a cell proliferative disorder such as actinic keratosis, arteriosclerosis, atherosclerosis, bursitis. cirrhosis, hepatitis, mixed connective tissue disease (MCTD), psoriasis, primary thrombocythemia, and cancers including adenocarcinoma, leukemia, lymphoma, melanoma, myeloma, sarcoma, teratocarcinoma, and, in particular, cancer of the colon; an immune disorder such as inflammation, actinic keratosis, acquired immunodeficiency syndrome (AIDS), Addison's disease, adult respiratory distress syndrome, allergies, anemia, asthma, autoimmune thyroiditis, bronchitis, bursitis, cholecystitis, cirrhosis, contact dermatitis, Crohn's disease, diabetes mellitus, emphysema, gout, Graves' disease, hepatitis, hypereosinophilia, irritable bowel syndrome, multiple sclerosis, myasthenia gravis, myocardial or pericardial inflammation, osteoarthritis, osteoporosis, pancreatitis, rheumatoid arthritis, scleroderma, and ulcerative colitis; and a cell signaling disorder including endocrine disorders such as disorders of the hypothalamus and pituitary resulting from lesions such as primary brain tumors, adenomas, hypophysectomy, aneurysms, vascular malformations, thrombosis, and complications due to head trauma; disorders associated with hyperpituitarism including acromegaly, giantism, and syndrome of inappropriate antidiuretic hormone (ADH) secretion (SIADH); disorders associated with hypothyroidism including goiter, myxedema, acute thyroiditis associated with bacterial infection; and disorders associated with hyperparathyroidism including Conn disease (chronic hypercalemia).

In another embodiment, a pharmaceutical composition comprising a substantially purified mammalian protein in conjunction with a pharmaceutical carrier may be administered to a subject to treat or prevent a condition associated with altered expression or activity of the endogenous protein including, but not limited to, those provided above.

In a further embodiment, a ligand which modulates the activity of the mammalian protein may be administered to a subject to treat or prevent a condition associated with altered lifespan, expression, or activity of the protein including, but not limited to, those listed above. In one aspect, an antibody which specifically binds the mammalian protein may be used as a targeting or delivery mechanism for bringing a pharmaceutical agent to cells or tissue that express the mammalian protein.

In an additional embodiment, a vector capable of expressing the mammalian protein or a portion or derivative thereof may be administered to a subject to treat or prevent a condition associated with altered lifespan, expression, or activity of protein including, but not limited to, those described above.

In a still further embodiment, a vector expressing the complement of the nucleic acid molecule or fragments thereof may be administered to a subject to treat or prevent a condition associated with altered lifespan, expression, or activity of the protein including, but not limited to, those described above.

Any of the nucleic acid molecules, complementary molecules and fragments thereof, proteins or portions thereof, vectors delivering these nucleic acid molecules or proteins, and their ligands may be administered in combination with other therapeutic agents. Selection of the agents for use in combination therapy may be made by one of ordinary skill in the art according to conventional pharmaceutical principles. A combination of therapeutic agents may act synergistically to affect prevention or treatment of a particular condition at a lower dosage of each agent.

Modification of Gene Expression Using Nucleic Acids

Gene expression may be modified by designing complementary or antisense molecules (DNA, RNA, or PNA) to the control, 5', 3', or other regulatory regions of the mammalian gene. Oligonucleotides designed with reference to the transcription initiation site are preferred. Similarly, inhibition can be achieved using triple helix base-pairing that inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and mRNA. In one alternative, a library of nucleic acid molecules or fragments thereof may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features that would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio-groups renders the molecule less available to endogenous endonucleases.

Screening Assays

The nucleic acid molecule encoding the mammalian protein may be used to screen a library of molecules or compounds for specific binding affinity. The libraries may be DNA molecules, RNA molecules, PNAs, peptides, proteins such as transcription factors, enhancers, repressors, and other ligands that regulate the activity, replication, transcription, or translation of the nucleic acid molecule in the biological system. The assay involves combining the mammalian nucleic acid molecule or a fragment thereof with the library of molecules under conditions allowing specific binding, and detecting specific binding to identify at least one molecule that specifically binds the nucleic acid molecule.

Similarly the mammalian protein or a portion thereof may be used to screen libraries of molecules or compounds in any of a variety of screening assays. The portion of the protein employed in such screening may be free in solution, affixed to an abiotic or biotic substrate (e.g. borne on a cell surface), or located intracellularly. Specific binding between the protein and molecule may be measured. Depending on the kind of library being screened, the assay may be used to identify DNA, RNA, or PNA molecules, agonists, antagonists, antibodies, immunoglobulins, inhibitors, peptides, proteins, drugs, or any other ligand, which specifically binds the protein. One method for high throughput screening using very small assay volumes and very small amounts of test compound is described in U.S. Pat. No. 5,876,946, incorporated herein by reference, which screens large numbers of molecules for enzyme inhibition or receptor binding.

Purification of Ligand

The nucleic acid molecule or a fragment thereof may be used to purify a ligand from a sample. A method for using a mammalian nucleic acid molecule or a fragment thereof to purify a ligand would involve combining the nucleic acid molecule or a fragment thereof with a sample under conditions to allow specific binding, detecting specific binding, recovering the bound nucleic acid molecule, and using an appropriate agent to separate the nucleic acid molecule from the purified ligand.

Similarly, the protein or a portion thereof may be used to purify a ligand from a sample. A method for using a mammalian protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor that ameliorates the symptoms or condition. Therapeutic efficacy and toxicity of such agents may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it may be expressed as the ratio, LD50/ED50. Pharmaceutical compositions that exhibit large therapeutic indexes are preferred. The data obtained from cell culture assays and animal studies are used in formulating a range of dosage for human use.

Model Systems

Animal models may be used as bioassays where they exhibit a toxic response similar to that of humans and where exposure conditions are relevant to human exposures. Mammals are the most common models, and most toxicity studies are performed on rodents such as rats or mice because of low cost, availability, and abundant reference toxicology. Inbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice to help predict the effects of these agents on human health. Observation of qualitative and quantitative changes in physiology, behavior, homeostatic processes, and lethality are used to generate a toxicity profile and to assess the consequences on human health following exposure to the agent.

Genetic toxicology identifies and analyzes the ability of an agent to produce genetic mutations. Genotoxic agents usually have common chemical or physical properties that facilitate interaction with nucleic acids and are most harmful when chromosomal aberrations are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle which produces the number of organisms needed to satisfy statistical requirements.

Acute toxicity tests are based on a single administration of the agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Prolonged toxicity tests are based on the repeated administration of the agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See U.S. Pat. Nos. 4,736,866; 5,175,383; and 5,767,337). In some cases, the introduced gene may be activated at a specific time in a specific tissue type during fetal development or postnatally. Expression of the transgene is monitored by analysis of phenotype or tissue-specific mRNA expression in transgenic animals before, during, and after challenge with experimental drug therapies.

Embryonic Stem Cells

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene that disrupts transcription and/or translation in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Transformed ES cells are identified, and preferably microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes (Bain et al.

(1995) Dev. Biol. 168:342–357; Wiles and Keller (1991) Development 111:259–267; and Klug et al. (1996) J. Clin. Invest. 98:216–224) Recent developments demonstrate that ES cells derived from human blastocysts may also be manipulated in vitro to differentiate into eight separate cell lineages, including endoderm, mesoderm, and ectodermal cell types (Thomson (1998) Science 282:1145–1147).

Knockout Analysis

In gene knockout analysis, a region of a human disease gene candidate is enzymatically modified to include a non-mammalian gene such as the neomycin phosphotransferase gene (neo; Capecchi (1989) Science 244:1288–1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudopregnant dams. Transgenic progeny are crossbred to obtain homozygous inbred lines.

Knockin Analysis

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells that contain the integrated human gene are handled as described above. Inbred animals are studied and treated to obtain information on the analogous human condition. These methods have been used to model several human diseases. (See, e.g., Lee et al. (1998) Proc. Nat). Acad. Sci. 95:11371–11376; Baudoin et al. (1998) Genes Dev. 12:1202–1216; and Zhuang et al. (1998) Mol. Cell Biol. 18:3340–3349.)

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus monkeys (*Macaca fascicularis, Macaca mulatta*) and common marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPS are the first choice test animal. In addition, NHPS and individual humans exhibit differential sensitivities to many drugs and toxins and can be classified as "extensive metabolizers" and "poor metabolizers" of these agents.

In additional embodiments, the nucleic acid molecules that encode the mammalian protein may be used in any molecular biology techniques that have yet to be developed, provided the new techniques rely on properties of nucleic acid molecules that are currently known, including, but not limited to, such properties as the triplet genetic code and specific base pair interactions.

EXAMPLES

It is to be understood that this invention is not limited to the particular machines, materials and methods described. Although particular embodiments are described, equivalent embodiments may be used to practice the invention. The described embodiments are not intended to limit the scope of the invention which is limited only by the appended claims. The examples below are provided to illustrate the subject invention and are not included for the purpose of limiting the invention. For purposes of example, the preparation of the human uterine tissue cDNA library, UTRSNOR01, is described.

I Representative cDNA Sequence Preparation

The UTRSNOR01 cDNA library was constructed from microscopically normal endometrium obtained from a 29-year-old Caucasian female (specimen #0909A) during a vaginal hysterectomy and cystocele repair. Pathology of the uterus indicated a single intramural uterine leiomyoma. The endometrium was in secretory phase, and the cervix showed mild chronic cervicitis with focal squamous metaplasia. Patient history included hypothyroidism, pelvic floor relaxation, an incomplete T-12 injury from a motor vehicle accident causing paraplegia, and self-catheterization. Family history included benign hypertension, diabetes type H, and hyperlipidemia.

The frozen tissue was homogenized and lysed in TRIZOL reagent (1 gm tissue/10 ml TRIZOL; Cat. #10296–028; Life Technologies, Gaithersburg Md.), a monoplastic solution of phenol and guanidine isothiocyanate, using a POLYTRON homogenizer (PT-3000; Brinkmann Instruments, Westbury N.Y.). After a brief incubation on ice, chloroform was added (1:5 v/v), and the lysate was centrifuged. The upper chloroform layer was removed to a fresh tube, and the RNA precipitated with isopropanol, resuspended in DEPC-treated water, and treated with DNase for 25 min at 37° C. The mRNA was re-extracted once with acid phenol-chloroform, pH 4.7, and precipitated using 0.3M sodium acetate and 2.5 volumes of ethanol. The mRNA was isolated with the OLIGOTEX kit (Qiagen, Chatsworth Calif.) and used to construct the cDNA library.

The mRNA was handled according to the recommended protocols in the SUPERSCRIPT plasmid system for cDNA synthesis and plasmid Cloning (Life Technologies). The cDNAs were fractionated on a SEPHAROSE CL4B column (Amersham Pharmacia Biotech), and those cDNAs exceeding 400 bp were ligated into pINCY 1 plasmid (Incyte Pharmaceuticals Palo Alto, Calif.). The plasmid was subsequently transformed into DH5α competent cells (Life Technologies).

II Isolation and Sequencing of cDNA Clones

Plasmid DNA was released from the cells and purified using the REAL Prep 96 plasmid kit (Qiagen). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were prepared using a MICROLAB 2200 (Hamilton, Reno, Nev.) in combination with a Peltier DNA ENGINE thermal cyclers ( MJ Research, Watertown, Mass.). The cDNAs were sequenced by the method of Sanger and Coulson (1975, J Mol Biol 94:441–448),) using an ABI PRISM 377 DNA Sequencing Systems (PE Biosystems), and the reading frame was determined.

III Identification, Extension, Assembly, and Analyses

The consensus sequence (SEQ ID NO:28) was assembled from Incyte Clones (library) 908465R2 (COLNNOT09), 957130R6 (KIDNNOT05), 1301520F6 (BRSTNOT07), 1580628H1 (DUODNOT01), 2631247F6 (COLNTUT15), 3068538H1 (UTRSNOR01), and 3532286T6 (KIDNNOT25) from the LIFESEQ database (Incyte Pharmaceuticals) of human cDNA sequences and used to identify additional sequences in the LIFESEQ and ZOOSEQ databases (Incyte Pharmaceuticals) related to GTPAP. Translation of SEQ ID NOs:28 and 29 using MACDNASIS PRO software (Hitachi Software Engineering) elucidated the coding regions, SEQ ID NOs:30 and 31, respectively.

The polynucleotide sequences derived from cDNA sequencing were assembled and analyzed using a combination of software programs which utilize algorithms well known to those skilled in the art. Table 1 summarizes the tools, programs, and algorithms used and provides applicable descriptions, references, and threshold parameters. The first column of Table 1 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score, the greater the homology between two sequences). Sequences were analyzed using MACDNASIS PRO software (Hitachi Software Engineering, South San Francisco Calif.) and LASERGENE software (DNASTAR).

The polynucleotide sequences were validated by removing vector, linker, and polyA sequences and by masking ambiguous bases, using algorithms and programs based on BLAST, dynamic programing, and dinucleotide nearest neighbor analysis. The sequences were then queried against a selection of public databases such as the GenBank primate, rodent, mammalian, vertebrate, and eukaryote databases, and BLOCKS, PRINTS, DOMO, PRODOM, and PFAM to acquire annotation using programs based on BLAST, FASTA, and BLIMPS. The sequences were assembled into full length polynucleotide sequences using programs based on Phred, PHRAP, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, DOMO, PRODOM, Prosite, and Hidden Markov Model (HMM)-based protein family databases such as PFAM. HMM is a probabilistic approach which analyzes consensus primary structures of gene families. (See, e.g., Eddy, S. R. (1996) Curr. Opin. Str. Biol. 6:361–365.)

The programs described above for the assembly and analysis of full length polynucleotide and amino acid sequences were also used to identify polynucleotide sequence fragments from SEQ ID NOs:28 and 29. Fragments from about 20 to about 4000 nucleotides which are useful in hybridization and amplification technologies were described in The Invention section above.

IV Identification of Nucleic Acid Variants

Nucleic acid molecules which are variants of the nucleic acid molecules encoding the mammalian GTPase-activating protein (SEQ ID NOs:28 and 29) were identified by using BLAST or BLAST2 (Altschul, supra; NCI-BLASTN version 2.0.4 with default parameters), to identify clones in the LIFESEQ or ZOOSEQ database (Incyte Pharmaceuticals) which aligned with SEQ ID NOs:28 and 29. Mammalian nucleic acid molecule variants were selected by BLAST score. The BLAST score is calculated by scoring +5 for every base that matches in a nucleic acid High Scoring Pair (HSP) and −4 for every mismatch. The BLAST alignments were visually inspected and those clones with BLAST scores greater than 100 were aligned together using PHRAP (Green, supra).

V Northern Analysis

Northern analysis is a laboratory technique used to detect the presence of a transcript of a gene and involves the hybridization of a labeled probe to a membrane on which RNAs from a particular cell type or tissue have been bound.

Analogous computer techniques applying BLAST2 (NCI-BLASTN version 2.0.4 with default parameters) were used to search for identical or related molecules in nucleotide databases such as the LIFESEQ database or ZOOSEQ database (both Incyte Pharmaceuticals). Sequence-based analysis is much faster than membrane-based hybridization, and the sensitivity of the computer search can be modified to determine whether any particular match is categorized as exact or similar. The basis of the BLAST search is the product score which is defined as: (percent sequence identity×percent maximum BLAST score) divided by 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

The results of northern analyses are reported as a fraction or a percentage distribution of libraries in which the transcript encoding the mammalian protein occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease categories included cancer, inflammation/trauma, cell proliferation, and neurological. For each category, the number of libraries expressing the sequence was counted and divided by the total number of libraries identified containing nucleic acid molecule variants of the nucleic acid molecule encoding the mammalian protein.

VI Extension of Nucleic Acid Molecules

At least one of the nucleic acid molecules used to assemble SEQ ID NOs:28 and 29 was produced by extension of an Incyte cDNA clone using oligonucleotide primers. One primer was synthesized to initiate 5' extension of the known fragment, and the other, to initiate 3' extension. The initial primers were designed using OLIGO 4.06 software (National Biosciences) to be about 22 to 30 nucleotides in length, to have a GC content of about 50%, and to anneal to the target sequence at temperatures of about 55° C. to about 68° C. Any fragment which would result in hairpin structures and primer-primer dimerizations was avoided. Selected human cDNA libraries were used to extend the molecule. If more than one extension is needed, additional or nested sets of primers are designed.

High fidelity amplification was obtained by performing PCR in 96-well plates using the DNA ENGINE thermal cycler (M J Research). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair selected from the plasmid: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, parameters for the primer pair, T7 and SK+ (Stratagene), were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7; storage at 4° C.

The concentration of DNA in each well was determined by dispensing 100 µl PICOGREEN quantitation reagent (0.25% (v/v); Molecular Probes) dissolved in 1×TE and 0.5 µl of undiluted PCR product into each well of an opaque fluorimeter plate (Corning Costar, Acton Mass.) and allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose mini-gel to determine which reactions were successful in producing longer sequence.

The extended sequences were desalted, concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested fragments were separated on about 0.6–0.8% agarose gels, fragments were excised as visualized under UV light, and agar removed/digested with AGARACE (Promega). Extended fragments were religated using T4 DNA ligase (New England Biolabs, Beverly Mass.) into pUC 18 vector (Amersham Pharmacia Biotech), treated with Pfu DNA polymerase (Stratagene) to fill-in restriction site overhangs, and transformed into competent *E. coli* cells. Transformed cells were selected on antibiotic-containing media, and individual colonies were picked and cultured overnight at 37° C. in 384-well plates in LB/2×carbenicillin liquid media.

The cells were lysed, and DNA was amplified using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the conditions described above. Samples were diluted with 20% dimethylsulfoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (PE Biosystems).

In like manner, a nucleic acid molecule of SEQ ID NOs:1–29 is used to obtain regulatory sequences using the procedure above, oligonucleotides designed for outward extension, and a genomic DNA library.

VII Hybridization Technologies and Analyses
Immobilization of Polynucleotides on a Substrate Polynucleotides are applied to a substrate by one of the following methods. A mixture of polynucleotides is fractionated by gel electrophoresis and transferred to a nylon membrane by capillary transfer. Alternatively, the polynucleotides are individually ligated to a vector and inserted into bacterial host cells to form a library. The polynucleotides are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37° C. for 16 hr. The membrane is removed from the agar and consecutively placed colony side up in 10% SDS, denaturing solution (1.5 M NaCl, 0.5 M NaOH ), neutralizing solution (1.5 M NaCl, 1 M Tris, pH 8.0), and twice in 2×SSC for 10 min each. The membrane is then UV irradiated in a STRATALINKER-UV-crosslinker (Stratagene).

In the second method, polynucleotides are amplified from bacterial vectors by thirty cycles of PCR using primers complementary to vector sequences flanking the insert. PCR amplification increases a starting concentration of 1–2 ng nucleic acid to a final quantity greater than 5 µg. Amplified nucleic acids from about 400 bp to about 5000 bp in length are purified using SEPHACRYL-400 beads (Amersham Pharmacia Biotech). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807,522. Polymer-coated slides are prepared by cleaning glass microscope slides (Corning, Acton Mass.) by ultrasound in 0.1% SDS and acetone, etching in 4% hydrofluoric acid (VWR Scientific Products, West Chester Pa.), coating with 0.05% aminopropyl silane (Sigma Aldrich) in 95% ethanol, and curing in a 110° C. oven. The slides are washed extensively with distilled water between and after treatments. The nucleic acids are arrayed onto the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in PBS (Tropix, Bedford Mass.) for 30 min at 60° C.; then the arrays are washed in 0.2% SDS and rinsed in distilled water as before.

Probe Preparation for Membrane Hybridization

Hybridization probes derived from the polynucleotides of the Sequence Listing are employed for screening cDNAs, mRNAs, or genomic DNA in membrane-based hybridizations. Probes are prepared by diluting the polynucleotides to a concentration of 40–50 ng in 45 µl TE buffer, denaturing by heating to 100° C. for five min, and briefly centrifuging. The denatured polynucleotide is then added to a REDIPRIME tube (Amersham Pharmacia Biotech), gently mixed until blue color is evenly distributed, and biefly centrifuged. Five microliters of [$^{32}$P]dCTP is added to the tube, and the contents are incubated at 37° C. for 10 min. The labeling reaction is stopped by adding 5 µl of 0.2M EDTA, and probe is purified from unincorporated nucleotides using a PROBEQUANT G-50 microcolumn (Amersham Pharmacia Biotech). The purified probe is heated to 100° C. for five min, snap cooled for two min on ice, and used in membrane-based hybridizations as described below.

Probe Preparation for Polymer Coated Slide Hybridization

Hybridization probes derived from mRNA isolated from samples are employed for screening polynucleotides of the Sequence Listing in array-based hybridizations. Probe is prepared using the GEMbright kit (Incyte Pharmaceuticals)

by diluting mRNA to a concentration of 200 ng in 9 µl TE buffer and adding 5 µl 5×buffer, 1 µl 0.1 M DTT, 3 µl Cy3 or Cy5 labeling mix, 1 µl RNase inhibitor, 1 µl reverse transcriptase, and 5 µl 1×yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37° C. for two hr. The reaction mixture is then incubated for 20 min at 85° C., and probes are purified using two successive CHROMA SPIN+TE 30 columns (Clontech). Purified probe is ethanol precipitated by diluting probe to 90 µl in DEPC-treated water, adding 2 µl 1 mg/ml glycogen, 60 µl 5 M sodium acetate, and 300 µl 100% ethanol. The probe is centrifuged for 20 min at 20,800×g, and the pellet is resuspended in 12 µl resuspension buffer, heated to 65° C. for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1×high phosphate buffer (0.5 M NaCl, 0.1 M $Na_2HPO_4$, 5 mM EDTA, pH 7) at 55° C. for two hr. The probe, diluted in 15 ml fresh hybridization solution, is then added to the membrane. The membrane is hybridized with the probe at 55° C. for 16 hr. Following hybridization, the membrane is washed for 15 min at 25° C. in 1 mM Tris (pH 8.0), 1% Sarkosyl, and four times for 15 min each at 25° C. in 1 mM Tris (pH 8.0). To detect hybridization complexes, XOMAT-AR film (Eastman Kodak, Rochester N.Y.) is exposed to the membrane overnight at −70° C., developed, and examined visually.

Polymer Coated Slide-based Hybridization

Probe is heated to 65° C. for five min, centrifuged five min at 9400 rpm in a 5415 C. microcentrifuge (Eppendorf Scientific, Westbury N.Y.), and then 18 µl is aliquoted onto the array surface and covered with a coverslip. The arrays are transferred to a waterproof chamber having a cavity just slightly larger than a microscope slide. The chamber is kept at 100% humidity internally by the addition of 140 µl of 5×SSC in a corner of the chamber. The chamber containing the arrays is incubated for about 6.5 hr at 60° C. The arrays are washed for 10 min at 45° C. in 1×SSC, 0.1% SDS, and three times for 10 min each at 45° C. in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to substantially equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of CyS. The excitation laser light is focused on the array using a 20×microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for CyS. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Pharmaceuticals).

VIII Complementary Nucleic Acid Molecules

Molecules complementary to the nucleic acid molecule, or a fragment thereof, are used to detect, decrease, or inhibit gene expression. Although use of oligonucleotides comprising from about 15 to about 30 base pairs is described, the same procedure is used with larger or smaller fragments or their derivatives (PNAs). Oligonucleotides are designed using OLIGO 4.06 software (National Biosciences) and SEQ ID NOs:1–29. To inhibit transcription by preventing promoter binding, a complementary oligonucleotide is designed to bind to the most unique 5' sequence, most preferably about 10 nucleotides before the initiation codon of the open reading frame. To inhibit translation, a complementary oligonucleotide is designed to prevent ribosomal binding to the mRNA encoding the mammalian protein.

IX Expression of the Mammalian Protein

Expression and purification of the mammalian protein are achieved using bacterial or virus-based expression systems. For expression in bacteria, cDNA is subcloned into a vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into bacterial hosts, e.g., BL21(DE3). Antibiotic resistant bacteria express the mammalian protein upon induction with isopropyl beta-D-thiogalactopyranoside (IPTG). Expression in eukaryotic cells is achieved by infecting *Spodoptera frugiperda* (Sf9) insect cells with recombinant baculovirus, *Autographica californica* nuclear polyhedrosis virus. The polyhedrin gene of baculovirus is replaced with the mammalian cDNA by either homologous recombination or bacterial-mediated transposition involving transfer plasmid intermediates. Viral infectivity is maintained and the strong polyhedrin promoter drives high levels of cDNA transcription.

In most expression systems, the mammalian protein is synthesized as a fusion protein with, e.g., GST or a peptide epitope tag, such as FLAG, permitting rapid, single-step, affinity-based purification of recombinant fusion protein from crude cell lysates. GST enables the purification of fusion proteins on immobilized glutathione under conditions that maintain protein activity and antigenicity (Amersham Pharmacia Biotech). Following purification, the GST moiety can be proteolytically cleaved from the mammalian protein at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (Qiagen). Methods for protein expression and purification are discussed in Ausubel (supra, unit 16). Purified mammalian protein obtained by these methods can be used directly in the following activity assay.

X Functional Assays

An assay for GTPAP activity measures the stimulation of intrinsic GTPase activity in a Rho GTPase. GTPase activity is using RhoA or Cdc42-GTPase is measured as described in Li et al. (1997) J Biol Chem 272:32830–32835. The assay is conducted in and absence of GTPAP and again in the presence of varying amounts of GTPAP. The amount of GTPase activity measured in the presence of GTPAP minus the amount measured in the absence of GTPAP is proportional to the activity of GTPAP in the sample.

In the alternative, protein function is assessed by expressing the sequences encoding GTPAP at physiologically elevated levels in mammalian cell culture. The nucleic acid molecule is subcloned into PCMV SPORT vector (Life Technologies), which contains the strong cytomegalovirus promoter, and 5–10 $\mu$g of the vector is transformed into a endothelial or hematopoietic human cell line using transformation methods well known in the art. An additional 1–2 $\mu$g of a plasmid containing sequence encoding CD64-GFP (Clontech, Palo Alto Calif.) is co-transformed to provide a fluorescent marker to identify transformed cells using flow cytometry (FCM).

The influence of the introduced genes on expression can be assessed using purified populations of these transformed cells. Since CD64-GFP, which is expressed on the surface of transformed cells, binds to conserved regions of human immunoglobulin G (IgG), the transformed cells are separated using magnetic beads coated with either human IgG or antibody against CD64 (DYNAL, Lake Success N.Y.). mRNA is purified from the cells and analyzed by hybridization techniques.

XI Production of GTPAP Specific Antibodies

GTPAP is purified using polyacrylamide gel electrophoresis and used to immunize mice or rabbits. Antibodies are produced using the protocols below. Alternatively, the amino acid sequence of GTPAP is analyzed using LASERGENE software (DNASTAR) to determine regions of high immunogenicity. An immunogenic epitope, usually found near the C-terminus or in a hydrophilic region is selected, synthesized, and used to raise antibodies. Typically, epitopes of about 15 residues in length are produced using an ABI Model 431A peptide synthesizer (PE Biosystems) using Fmoc-chemistry and coupled to KLH (Sigma-Aldrich) by reaction with N-maleimidobenzoyl-N-hydroxysuccinimide ester to increase immunogenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XII Purification of Naturally Occurring Protein Using Specific Antibodies

Naturally occurring or recombinant mammalian protein is substantially purified by immunoaffinity chromatography using antibodies specific for the protein. An immunoaffinity column is constructed by covalently coupling the antibody to CNBr-activated SEPHAROSE resin (Amersham Pharmacia Biotech). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIII Mapping of Polynucleotides to the Colon Cancer Region of Chromosome 22

Public domain genomic DNA sequence data for chromosome 22 was obtained from Genbank and was described in Dunham, I. et al. (1999) Nature 402:489–495. Incyte templates, including Incyte ID No. 440424.5 (SEQ ID NO:29), were aligned with the public domain genomic sequence using BLAST2 and a match between any two sequences was determined by a 98% identity over at least 100 bp. A region of chromosome 22 associated with colon cancer which was identified by Castells et al., supra is defined by the public domain sequence tagged sites D22S1171 and D22S92. These markers were aligned by BLAST2 with the sequence of chromosome 22 to determine the coordinates of genomic DNA associated with this region. Genomic DNA sequences which had been matched to SEQ ID NO:29 as described above was mapped within this region.

XIV Screening Molecules for Specific Binding with the Nucleic Acid Molecule or Protein The nucleic acid molecule, or fragments thereof, or the protein, or portions thereof, are labeled with $^{32}$P-dCTP, Cy3-dCTP, or Cy5-dCTP (Amersham Pharmacia Biotech), or with BIODIPY or FITC (Molecular Probes, Eugene Oreg.), respectively. Libraries of candidate molecules previously arranged on a substrate are incubated in the presence of labeled nucleic acid molecule or protein. After incubation under conditions for either a nucleic acid or amino acid sequence, the substrate is washed, and any position on the substrate retaining label, which indicates specific binding or complex formation, is assayed, and the binding molecule is identified. Data obtained using different concentrations of the nucleic acid or protein are used to calculate affinity between the labeled nucleic acid or protein and the bound molecule.

XV Identification of Molecules Which Interact with GTPAP

GTPAP, or biologically active portions thereof, are labeled with $^{125}$I Bolton-Hunter reagent (Bolton et al. (1973) Biochem. J. 133:529–539). Candidate ligand molecules previously arrayed in the wells of a multi-well plate are incubated with the labeled GTPAP, washed, and any wells with labeled GTPAP complex are assayed. Data obtained using different concentrations of GTPAP are used to calculate values for the number, affinity, and association of GTPAP with the candidate ligand molecules.

TABLE 1

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215:403–410; Altschul, S. F. et al. (1997) Nucleic Acids Res. 25: 3389–3402. | ESTs: Probability value = 1.0E–8 or less Full Length sequences: Probability value = 1.0E–10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85:2444–2448; Pearson, W. R. (1990) Methods Enzymol. 183: 63–98; and Smith, T. F. and M. S. Waterman (1981) Adv. Appl. Math. 2:482–489. | ESTs: fasta E value = 1.06E–6 Assembled ESTs: fasta Identity = 95% or greater and Match length = 200 bases or greater; fastx E value = 1.0E–8 or less Full Length sequences: fastx score = 100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S and J. G. Henikoff, Nucl. Acid Res., 19:6565–72, 1991. J. G. Henikoff and S. Henikoff (1996) Methods Enzymol. 266:88–105; and Attwood, T. K. et al. (1997) J. Chem. Inf. Comput. Sci. 37: 417–424. | Score = 1000 or greater; Ratio of Score/Strength = 0.75 or larger; and, if applicable, Probability value = 1.0E–3 or less |
| HMMER | An algorithm for searching a query sequence against hidden Markov model (HMM)-based databases of protein family consensus sequences, such as PFAM. | Krogh, A. et al. (1994) J. Mol. Biol., 235:1501–1531; Sonnhammer, E. L. L. et al. (1988) Nucleic Acids Res. 26:320–322. | Score = 10–50 bits for PFAM hits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25: 217–221. | Normalized quality score ≥ GCG-specified "HIGH" value for that particular Prosite motif. Generally, score = 1.4–2.1. |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2:482–489; Smith, T. F. and M. S. Waterman (1981) J. Mol. Biol. 147:195–197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claverie, J. M. and S. Audic (1997) CABIOS 12: 431–439. | Score = 3.5 or greater |
| Motifs | A program that searches amino acid sequences for patterns that matched those defined in Prosite. | Bairoch et al. supra; Wisconsin Package Program Manual, version 9, page M51–59, Genetics Computer Group, Madison, WI. | |

What is claimed is:

1. An isolated nucleic acid molecule, or the complete complement thereof, encoding a protein comprising an amino acid sequence of SEQ ID NO:30.

2. A variant of the nucleic molecule of claim 1, wherein said variant encodes the amino acid sequence of SEQ ID NO:31.

3. An isolated nucleic acid molecule comprising a sequence of SEQ ID NO:28 or SEQ ID NO:29, or the complete complement thereof.

4. A probe comprising the polynucleotide of claim 3.

5. A variant of the nucleic acid molecule of claim 1 comprising a nucleic acid sequence of SEQ ID NO:28 containing at least one single nucleotide polymorphism selected from:
   a) A or T at nucleotide 661 of SEQ ID NO:28,
   b) C or T at nucleotide 1012 of SEQ ID NO:28, and
   c) C or G at nucleotide 1019 of SEQ ID NO:28.

6. A recombinant nucleic acid molecule comprising a promoter operably linked to the nucleic acid molecule of claim 3.

7. A cell transformed with the recombinant nucleic acid molecule of claim 6.

8. A method of producing a polypeptide, the method comprising:
   a) culturing the cell of claim 7 under conditions for expression of the polypeptide, and
   b) recovering the polypeptide so expressed.

9. A method for detecting a nucleic acid molecule in a sample, the method comprising:
   a) hybridizing the sample with the probe of claim 4 to form a hybridization complex; and
   b) detecting hybridization complex formation, wherein formation of the hybridization complex indicates the presence of the nucleic acid molecule in the sample.

10. The method of claim 9 further comprising amplifying the nucleic acid molecule prior to hybridization.

11. A method of using a nucleic acid molecule to screen a library of molecules to identify at least one ligand that specifically binds the nucleic acid molecule, the method comprising:
    a) combining the nucleic acid molecule of claim 3 with the library of molecules under conditions to allow specific binding, and
    b) detecting specific binding, thereby identifying a ligand that specifically binds the nucleic acid molecule.

12. The method of claim 11 wherein the library is selected from DNA molecules, RNA molecules, PNAs, peptides, and proteins.

13. A method of using a nucleic acid molecule to purify a ligand that specifically binds the nucleic acid molecule from a sample, the method comprising:
    a) combining the nucleic acid molecule of claim 3 with a sample under conditions to allow specific binding;
    b) recovering the bound nucleic acid molecule; and
    c) separating the nucleic acid molecule from the ligand, thereby obtaining purified ligand.

* * * * *

UNITED STATES PATENT AND TRADEMARK OFFICE
CERTIFICATE OF CORRECTION

PATENT NO. : 6,509,155 B1
DATED : January 21, 2003
INVENTOR(S) : Klinger et al.

It is certified that error appears in the above-identified patent and that said Letters Patent is hereby corrected as shown below:

Column 63,
Line 31, replace claim 4 with -- 4. A probe comprising the isolated nucleic acid molecule of claim 3. --

Signed and Sealed this

Twenty-fifth Day of May, 2004

JON W. DUDAS
*Acting Director of the United States Patent and Trademark Office*